(12) United States Patent
England

(10) Patent No.: US 7,462,155 B2
(45) Date of Patent: Dec. 9, 2008

(54) OBJECTIVE DETERMINATION OF CHRONIC PAIN IN PATIENTS

(76) Inventor: Robert L. England, 1443 Tamara Ct., Benicia, CA (US) 94510

( * ) Notice: Subject to any disclaimer, the term of this patent is extended or adjusted under 35 U.S.C. 154(b) by 512 days.

(21) Appl. No.: 10/975,237

(22) Filed: Oct. 27, 2004

(65) Prior Publication Data

US 2006/0089551 A1    Apr. 27, 2006

(51) Int. Cl.
*A61B 19/00* (2006.01)
*A61B 5/05* (2006.01)
*A61B 5/04* (2006.01)
*A61B 5/00* (2006.01)

(52) U.S. Cl. ................ 600/557; 600/407; 600/410; 600/425; 600/544; 600/552; 600/555

(58) Field of Classification Search ............ 600/544, 600/552–555, 557
See application file for complete search history.

(56) References Cited

U.S. PATENT DOCUMENTS

| | | | |
|---|---|---|---|
| 5,755,675 A | 5/1998 | Sihvonen | |
| 5,806,522 A | 9/1998 | Katims | |
| 5,818,231 A | 10/1998 | Smith | |
| 6,018,675 A | 1/2000 | Apkarian et al. | |
| 6,113,552 A | 9/2000 | Shimazu et al. | |

(Continued)

FOREIGN PATENT DOCUMENTS

| | | |
|---|---|---|
| WO | WO 94/13196 A1 | 6/1994 |
| WO | WO 02/02008 A1 | 1/2002 |
| WO | WO 2007/061807 A2 | 5/2007 |
| WO | WO 2007/064711 A2 | 6/2007 |

OTHER PUBLICATIONS

"Functional Magnetic Resonance Imaging: An Introductory Course;" Jun. 3-5, 2004; 6 pages; Functional Imaging Research Center; Medical College of Wisconsin.

(Continued)

*Primary Examiner*—Max Hindenburg
*Assistant Examiner*—H. Q. Nguyen
(74) *Attorney, Agent, or Firm*—Townsend and Townsend and Crew LLP

(57) ABSTRACT

A method for objectively determining if a patient suffers chronic pain by initially observing a multiplicity of persons who are free of chronic pain and subjecting them to a given pain stimulus. Radiofrequency (RF) emissions generated by the brains of the persons who are free of chronic pain while they are subjected to the pain stimulus are measured and a chart in the form of an average f-MRI image for all such persons is prepared which statistically reflects an average of RF emissions generated by the brains of the persons who are free of chronic pain while subjected to the pain stimulus. The same pain stimulus is then applied to the patient, RF emissions generated by a brain of the patient while the pain stimulus is applied are sensed, and the RF emissions from the patient's brain are compared to the chart to determine if the RF emissions from the patient's brain are statistically different from the approximately average RF emissions from the persons who are free of chronic pain on the chart. If so, it can be concluded without any conscious input from the patient that the patient suffers chronic pain. The method can be used to verify insurance or other compensation claims by persons who assert that they suffer chronic pain that might prevent them from performing certain functions such as work.

38 Claims, 2 Drawing Sheets

U.S. PATENT DOCUMENTS

| | | | |
|---|---|---|---|
| 6,146,334 | A | 11/2000 | Laserow |
| 6,907,280 | B2* | 6/2005 | Becerra et al. ............. 600/407 |
| 2002/0042563 | A1 | 4/2002 | Becerra et al. |
| 2002/0107434 | A1 | 8/2002 | Lange et al. |
| 2002/0111754 | A1 | 8/2002 | Lange et al. |
| 2002/0128798 | A1 | 9/2002 | Lange et al. |
| 2002/0138018 | A1 | 9/2002 | Lange et al. |
| 2003/0204148 | A1 | 10/2003 | Lange et al. |
| 2003/0225326 | A1* | 12/2003 | Querleux et al. ............. 600/407 |

OTHER PUBLICATIONS

"The Medical Examiner," Jan. 2001; 1 page; vol. 6; No. 1; California Industrial Medical Council Abram, et al.: *Pain Clinic Manual*: Oct. 1999; 496 pages; Lippincott Williams & Wilkins.

Alpar, et al., "Management of chronic pain in whiplash injury" *J Bone Joint Surg Br*. 84(6):807-11 (Aug. 2002).

Anderson, "The Future of the Cervical Spine" 28(24):2645-2647 (2003).

Andersson, et al.; "18.7 Malingering; *Guides to the Evaluation of Permanent Impairment*;" Dec. 15, 2000; pp. 585-586; Fifth Edition; American Medical Association.

Anzai, et al., "Epidural application of nucleus pulposus enhances nociresponses of rat dorsal horn neurons" *Spine* 27(3):E50-5 (Feb. 1, 2002).

Aoki, et al., Local Application of Disc-Related Cytokines on Spinal Nerve Roots *Spine* 27(15):1614-1617 (2002).

Apkarian, et al., "Chronic pain patients are impaired on an emotional decision-making task" *Pain* 108:129-136 (2004).

Apkarian, et al.; "Cortical Responses to Thermal Pain Depend on Stimulus Size: A Functional MRI Study;" *The Journal of Neurophysiology*; May 2000; pp. 3113-3122; vol. 83; No. 5; The American Physiological Society.

Apkarian, et al., "Differentiating Cortical Areas Related to Pain Perception From Stimulus Identification: Temporal Analysis of fMRI Activity" *Journal of Neurophysiology* 81:2956-2963 (1999).

Apkarian, "Functional Magnetic Resonance Imaging of Pain Consciousness: Cortical Networks of Pain Critically Depend on What is Implied by "Pain"" *Curr Rev Pain*. 3(4):308-315 (1998).

Apkarian, et al., "Imaging the pain of low back pain: functional magnetic resonance imaging in combination with monitoring subjective pain perception allows the study of clinical pain states" *Neurosciences Letters* 299:57-60 (2001).

Apkarian, et al.; "Persistent Pain Inhibits Contralateral Somatosensory Cortical Activity in Humans;" *Neurosci Lett*.; Jun. 22, 1992; pp. 141-147; vol. 140; No. 2; abstract.

Apkarian, et al.; "Prefrontal cortical hyperactivity in patients with sympathetically mediated chronic pain;" *Neurosci Lett*.; Oct. 5, 2001; pp. 193-197; vol. 311; No. 3; abstract.

Arendt-Nielsen, et al.; "Central sensitization in fibromyalgia and other musculoskeletal disorders;" *Curr Pain Headache Rep*. Oct. 2003;7(5):355-61; abstract.

Arnst, et al. "Conquering Pain: New discoveries and treatments offer hope;" *BusinessWeek*; Mar. 1, 1999; 8 pages.

Aronoff, et al., "Pain: psychiatric aspects of impairment and disability" *Curr Pain Headache Rep*. 7(2):105-15 (Apr. 2003).

Atcheson, et al., "Rapid resolution of chronic sciatica with intravenous infixlmab after failed epidural steroid injections" *Spine* 29(12):E248-50 (Jun. 15, 2004).

Atlas, et al.; "The Maine Lumbar Spine Study, Part III. 1-year outcomes of surgical and nonsurgical management of lumbar spinal stenosis;" *Spine*. Aug. 1, 1996;21(15):1787-94; discussion 1794-5; abstract.

Backonja, et al.; "Pharmacologic Management Part 1: Better-Studied Neuropathic Pain Diseases;" *Pain Med*; Mar. 2004; pp. s28-s47; vol. 5; Supplement 1; Abstract.

Ballas, et al.; "Medically unexplained physical symptoms: toward an alternative paradigm for diagnosis and treatment;" *CNS Spectr*. Dec. 2003;8(12 Suppl 3):20-6; abstract.

Bantick, et al., "Imaging how attention modulates pain in humans using functional MRI" *Brain* vol. 125(2):310-319 (Feb. 1, 2002).

Baron, et al.; "Brain processing of capsaicin-induced secondary hyperalgesia: a functional MRI study;" *Neurology*; Aug. 11, 1999; pp. 548-557; vol. 53; No. 3; abstract.

Becerra, et al., "Human brain activation under controlled thermal stimulation and habituation to noxious heat: an fMRI study" *Magn Reson Med*. 41(5):1044-57 (May 1999).

Biering-Sorensen, et al., "Medical, social and occupational history as risk indicators for low-back trouble in a general population" *Spine* 11(7):720-5 (Sep. 1986).

Biering-Sorensen, et al., "Risk indicators of disability pension. A 15 year follow-up study" *Dan Med Bull*. 46(3):258-62 (Jun. 1999).

Bingel, et al., "Single trial fMRI reveals significant contralateral bias in responses to laser pain within thalamus and somatosensory cortices" *Neuroimage* 18(3):740-8 (Mar. 2003).

Binzer, M. et al., "Clinical characteristics of patients with motor disability due to conversion disorder: a prospective control group study" *J Neurol Neurosurg Psychiatry* 63(1):83-8 (Jul. 1997).

Birket-Smith; "Somatization and chronic pain;" *Acta Anaesthesiol Scand*. Oct. 2001;45(9):1114-20; abstract.

Bluestone; "Fibromyalgia in the Clinic and Rheumatology Office;" *Position Paper on Fibromyalgia in the Workplace*; May 1999; 9 pages; Rodney Bluestone Medical Corporation.

Blyth, et al., "Chronic pain, work performance and litigation" *Pain* 103(1-2):41-7 (May 2003).

Boden, et al., "Abnormal magnetic-resonance scancs of the lumbar spine in asymptomatic subjects. A prospective investigation;" *J Bone Joint Surg Am*. Mar. 1990;72(3):403-8; abstract.

Boden, et al., "Abnormal magnetic-resonance scans of the cervical spine in asymptomatic subjects. A prospective investigation" *J Bone Joint Surg Am*. 72(8):1178-84 (Sep. 1990).

Boline, et al.; "Interexaminer Reliability and Discriminant Validity of Inclinometric Measurement of Lumbar Rotation in Chronic Low-Back Pain Patients and Subjects without Low-Back Pain;" *Spine*; Mar. 1992; pp. 335-338; vol. 17; No. 3; Abstract.

Borenstein, et al., "The value of magnetic resonance imaging of the lumbar spine to predict low-back pain in asymptomatic subjects : a seven-year follow-up study" *J Bone Joint Surg Am*. 83-A(9):1306-11 (Sep. 2001).

Borg-Stein; "Management of peripheral pain generators in fibromyalgia;" *Rheum Dis Clin North Am*. May 2002;28(2):305-17; abstract.

Bosk; "Forgive and Remember: Managing Medical Failure;" *JAMA*; Apr. 14, 2004; pp. 1775; vol. 291; No. 14.

Bouin, et al., "Pain hypersensitivity in patients with functional gastrointestinal disorders: a gastrointestinal-specific defect or a general systemic condition?" *Dig Dis Sci*. 46(11):2542-8 (Nov. 2001).

Bozzao, et al., "Lumbar disk herniation: MR imaging assessment of natural history in patients treated without surgery" *Radiology* 185(1):135-41 (Oct. 1992).

Brisby, et al., "Nitric oxide as a mediator of nucleus pulposus-induced effects on spinal nerve roots" *J Orthop Res* 18(5):815-20 (Sep. 2000).

Brown, et al.; "Hippocampal volume, spectroscopy, cognition, and mood in patients receiving corticosteroid therapy" *Biol Psychiatry* 55(5):538-45 (Mar. 1, 2004).

Buchel, et al.; "Interactions Among Neuronal Systems Assessed with Functional Neuroimaging;" *Rev Neurol*; Sep. 2001; pp. 807-815; vol. 157; 8-9 Part 1; Paris; Abstract.

Buirski, et al., "The symptomatic lumbar disc in patients with low-back pain. Magnetic resonance imaging appearances in both a symptomatic and control population" *Spine* 18(13):1808-11 (Oct. 1, 1993).

Burns, et al., "Association between workers' compensation and outcome following multidisciplinary treatment for chronic pain: roles of mediators and moderators" *Clin J Pain* 11(2):94-102 (Jun. 1995).

Bushnell, et al., "Pain perception: is there a role for primary somatosensory cortex?" *Proc Natl Acad Sci U S A* 96(14):7705-9 (Jul. 6, 1999).

Cabeza; "Cognitive Neuroscience of Aging: Contributions of Functional Neuroimaging;" *Scand J Psychol*; Jul. 2001; vol. 42; No. 3; Abstract.

Cailliet; *Low Back Disorders: A Medical Enigma*; Mar. 2003; 175 pages; Lippincott Williams & Wilkins.

Carli, et al.; "Reactivity to superficial and deep stimuli in patients with chronic musculoskeletal pain;" *Pain*. Dec. 2002;100(3):259-69; abstract.

Carragee, et al., "2000 Volvo Award winner in clinical studies: Lumbar high-intensity zone and discography in subjects without low back problems" *Spine* 25(23):2987-92 (Dec. 1, 2000).

Carragee, et al.; "False-positive findings on lumbar discography. Reliability of subjective concordance assessment during provocative disc injection;" *Spine*. Dec. 1, 1999;24(23):2542-7; abstract.

Carragee, "Is lumbar discography a determinate of discogenic low back pain: provocative discography reconsidered" *Curr Rev Pain* 4(4):301-8 (2000).

Carroll, et al.; "Absolute Quantification of Cerebral Blood Flow with Magnetic Resonance, Reproducibility of the Method, and Comparison with $H_2(15)O$ Positron Emission Tomography;" *J Cereb Blood Flow Metab.*; Sep. 2002; pp. 1149-1156; vol. 22; No. 9; Abstract.

Casey, et al., "Insights into the pathophysiology of neuropathic pain through functional brain imaging" *Experimental Neurology* 184:580-588 (2003).

Cassisi, et al., "Pain, disability, and psychological functioning in chronic low back pain subgroups: myofascial versus herniated disc syndrome" *Neurosurgery* 33(3):379-85; discussion 385-6 (Sep. 1993).

Centeno, et al.; "Waddell's signs revisited?;" *Spine*, Jul. 1, 2004;29(13):1392.

Chang, et al., "A fMRI study of brain activations during non-noxious and noxious electrical stimulation of the sciatic nerve of rats" *Brain Res.* 897(1-2):71-81 (Apr. 6, 2001).

Chen; et al.; "Differentiating Noxious- and Innocuous- Related Activation of Human Somatosensory Cortices Using Temporal Analysis of fMRI;" *The Journal of Neurophysiology*; Jul. 2002; pp. 464-474; vol. 88; No. 1; The American Physiological Society.

Chen, et al.; "Nervous System Reorganization Following Injury;" *Neuroscience*; 2002; pp. 761-773; vol. 111; No. 4; abstract.

Cherkin, et al., "Physician variation in diagnostic testing for low back pain. Who you see is what you get" *Arthritis Rheum* 37(1):15-22 (Jan. 1994).

Coghill, et al., "Distributed processing of pain and vibration by the human brain" *J Neurosci*. 14(7):4095-108 (Jul. 1994).

Coghill, et al., "Neural correlates of interindividual differences in the subjective experience of pain" *Proc Natl Acad Sci U S A* 100(14):8538-8542 (Jul. 8, 2003).

Coghill, et al., "Pain Intensity Processing Within the Human Brain: A Bilateral, Distributed Mechanism" *J Neurophysiol* 82:1934-1943 (1999).

Cohen, et al., "Signal detection and threshold measures to loud tones and radiant heat in chronic low back pain patients and cohort controls" *Pain* 16(3):245-52 (Jul. 1983).

Cook, et al.; "Functional imaging of pain in patients with primary fibromyalgia;" *J Rheumatol*. Feb. 2004;31(2):364-78; abstract.

Cox, "Medical College of Wisconsin Analysis of Functional NeuroImages" *MCW AFNI—User Manual* Version 2.00 (Dec. 1996).

Creac'h, et al.; "Functional MR imaging analysis of pain-related brain activation after acute mechanical stimulation;" *AJNR Am J Neuroradiol*. Sep. 2000;21(8):1402-6.

Croft, et al.; "More pain, more tender points: is fibromyalgia just one end of a continuous spectrum?;" *Ann Rheum Dis*. Jul. 1996;55(7):482-5; abstract.

Crombez, et al.; "Hypervigilance yo Pain in Fibromyalgia: The Mediating Role of Pain Intensity and Catastrophic Thinking About Pain;" *Clin J Pain*; Mar.-Apr. 2004; pp. 98-102; vol. 20; No. 2; Abstract.

Curatolo, et al., "Central Hypersensitivity in Chronic Pain After Whiplash Injury" *The Clinical Journal of Pain* 17:306-315 (2001).

Curran, et al.; "Altered response to tryptophan supplementation after long-term abstention from MDMA (ecstasy) is highly correlated with human memory function;" Psychopharmacology (Berl). Aug. 2003;169(1):91-103. Epub May 21, 2003; abstract.

Cyriax; *Textbook of Orthopaedic Medicine: Diagnosis of Soft Tissue Lesions*; Jan. 1, 1982; pp. 31-36 and 454; vol. 1; Eighth Edition; Baillierre Tindall.

Czeh, et al., "Stress-induced changes in cerebral metabolites, hippocampal volume, and cell proliferation are prevented by antidepressant treatment with tianeptine" *Proc Natl Acad Sci U S A* 98(22):12796-801 (Oct. 23, 2001).

Darre, et al., "[Back problems during military service—significance for later back problems. A 12-year follow-up study]" *Ugeskr Laeger* 161(13):1926-30 (Mar. 29, 1999).

Davis, et al., "Event-relatd fMRI of pain: entering a new era in imaging pain" *Neuroreport* 9(13):3019-23 (Sep. 1998).

Davis, et al., "fMRI of human somatosensory and cingulated cortex during painful electrical nerve stimulation" *Neuroreport* 7(1):321-5 (Dec. 29, 1995).

Davis, et al.; "Functional MRI of Pain- and Attention-Related Activations in the Human Cingulate Cortex;" *J Neurophysiol*; Jun. 1997; pp. 3370-3380: vol. 77; No. 6; Abstract.

Davis, et al., "Functional MRI Study of Thalamic and Cortical Activations Evoked by Cutaneous Heat, Cold, and Tactile Stimuli" *J Neurophysiol* 80:1533-1546 (1988).

Davis, et al., "Thalamic stimulation-evoked sensations in chronic pain patients and in nonpain (movement disorder) patients" *Journal of Neurophysiology* 75(3):1026-1037 (1996).

Davis, "The neural circuitry of pain as explored with functional MRI" *Neurological Research* vol. 22:313-317 (2000).

De Laat, et al.; "Correlation Between Cervical Spine and Temporomandibular Disorders;" *Clin Oral Investig*; Jun. 1998; pp. 54-57; vol. 2; No. 2; Abstract.

Derbyshire, et al., "Cerebral responses to a continual tonic pain stimulus measured using positron emission tomography" *Pain* 76(1-2):127-35 (May 1998).

Derbyshire, et al.; "Cerebral responses to noxious thermal stimulation in chronic low pack pain patients and normal controls;" *Neuroimage*. May 2002;16(1):158-68; abstract.

Derbyshire, "Measuring our natural painkiller" *Trends Neurosci*. 25(2):678; discussion 69 (Feb. 2002).

Dettmers, et al.: "Quantitative Comparison of Functional Magnetic Resonance Imaging with Positron Emission Tomography Using a Force-Related Paradigm;" *Neuroimage*; Dec. 1996; pp. 201-209; vol. 4; 3 Part 1; Abstract.

Devers, et al., "Topical Lidocaine Patch Relieves a Variety of Neuropathic Pain Conditions: An Open-Label Study" *The Clinical Journal of Pain* 16:205-208 (2000).

Dick, et al., "Attentional Functioning in Fibromyalgia, Rheumatoid Arthritis, and Musculoskeletal, Pain Patients" *Arthritis & Rheumatism* 47(6):639-644 (Dec. 15, 2002).

Disbrow, et al., "Somatosensory cortex: a comparison of the response to noxious thermal, mechanical, and electrical stimuli using functional magnetic resonance imaging" *Hum Brain Mapp*. 6(3):150-9 (1998).

Donoghue; "Plasticity of adult sensorimotor representations;" *Curr Opin Neurobiol*. Dec. 1995;5(6):749-54; abstract.

Dowman, et al., "Evidence that the anterior cingulated and supplementary somatosensory cortices generate the pain-related negative difference potential" 110(12):2117-26 (Dec. 1999).

Downar, et al., "Neural correlates of the prolonged salience of painful stimulation" *NeuroImage* 20:1540-1551 (2003).

Dvir: *Clinical biomechanics*: 2000; pp. 35, 54-57, 65, 79-81, 103, 122-125, 136-139; Churchill Livingstone.

Dvir, et al., "Maximal versus feigned active cervical motion in healthy patients: the coefficient of variation as an indicator for sincerity of effort" *Spine* 26(15):1680-8 (Aug. 1, 2001).

Dvir, et al., "The effects of protocol and test situation on maximal vs. submaximal cervical motion: medicolegal implicaitons" *Int J Legal Md* 117(6):350-5 (Dec. 2003) (Epug Oct. 2003).

Dworkin, et al., "Unraveling the effects of compensation, litigation, and employment on treatment response in chronic pain" *Pain* 23(1):49-59 (Sep. 1985).

Eck, et al., "Biomechanical study on the effect of cervical spine fusion on adjacent-level intradiscal pressure and segmental motion" *Spine* 27(22):2431-4 (Nov. 15, 2002).

Elliott, et al.; "Axonal Processes and Neural Plasticity. II: Adult Somatosensory Maps;" *Cereb Cortex*; Nov.-Dec. 1996; pp. 789-793; vol. 6; No. 6; abstract.

Erricsson, et al., "Depression predicts disability in long-term chronic pain patients" *Disability and Rehabilitation* 24(6):334-340 (2002).

Eulitz, et al.; "Intra-subject replication of brain magnetic activity during the processing of speech sounds;" *Brain Res Cogn Brain Res*, Mar. 2004;19(1):82-91; abstract.

Faggin, et al., "Immediate and simultaneous sensory reorganization at cortical and subcortical levels of the somatosensory system" *Proc. Natl. Acad. Sci. USA* 94:9428-9433 (Aug. 1997).

Fassbender, et al., "Tender points, depressive and functional symptoms: comparison between fibromyalgia and major depression" *Clin Rheumatol* 16(1):760-9 (Jan. 1977).

Faymonville, et al.; "Neural Mechanisms of Antinociceptive Effects of Hypnosis;" *Anesthesiology*; May 2000; pp. 1257-1267; vol. 92; No. 5; Abstract.

Feng, et al.; "CBF Changes During Brain Activation: fMRI vs. PET;" *Neuroimage*; May 2004; pp. 443-446; vol. 22; Issue 1; Abstract.

Feng, et al.; "Dynamic changes in the cerebral metabolic rate of O2 and oxygen extraction ratio in event-related functional MRI;" *Neuroimage*, Feb. 2003;18(2):257-62; abstract.

Ferguson, et al.; "Revised Protocol for the Kinematic Assessment of Impairment;" *Spine J.*; Mar.-Apr. 2004; pp. 163-169; vol. 4; No. 2; Abstract.

Fishbain, et al.; "A Structured Evidence-based Review on the Meaning of Nonorganic Physical Signs: Waddell Signs;" *Pain Med*; Jun. 2003; 2 pages; vol. 4; No. 2.

Fishbain, et al.; "Chronic pain disability exaggeration/malingering and submaximal effort research;" *Clin J Pain*. Dec. 1999;15(4):244-74; abstract.

Fishbain, et al.; "Do Antidepressants Have an Analgesic Effect in Psychogenic Pain and Somatoform Pain Disorder? A Meta-Analysis;" *Psychosom Med*; Jul.-Aug. 1998; pp. 503-509; vol. 60: No. 4: Abstract.

Fitzek, et al., "Event-related fMRI with painful electrical stimulation of the trigeminal nerve" *Magnetic Resonance Imaging* 22:205-209 (2004).

Flax, "Myofascial pain syndromes—the great mimicker" *Bol Asoc Med P R* 87(10-12):167-70 (Oct.-Dec. 1995).

Flor, "Cortical Reorganisation and Chronic Pain: Implications for Rehabilitation" *J Rehabil Med Suppl*. 41:66-72 (2003).

Forseth, et al.; "A 5.5 year prospective study of self-reported musculoskeletal pain and of fibromyalgia in a female population: significance and natural history;" *Clin Rheumatol*. 1999;18(2):114-21; abstract.

Forster, et al., "Functional magnetic resonance imaging: the basics of blood-oxygen-level dependent (BOLD) imaging" *Can Assoc Radiol J*. 49(5):320-9 (Oct. 1998).

Fritz, et al., "The use of nonorganic signs and symptons s a screening tool for return-to-work inpatients with acute low back pain" *Spine* 25(15):595 (Mar. 1, 2001).

Fulbright, et al.; "Functional MR Imaging of Regional Brain Activation Associated with the Affective Experience of Pain;" *AJR Am J Roentgenol*; Nov. 2001; pp. 1205-1210; vol. 177; No. 5.

Gaines, Jr., et al., "Effectiveness of Waddell's nonorganic signs in predicting a delayed return to regular work in patients experiencing acute occupational low back pain" *Spine* 24(4):396-400 (Feb. 15, 1999).

Ganis, et al., "Neural Correlates of Different Types of Deception: An fMRI Investigation" *Cerebral Cortex* 13:830-836 (Aug. 2003).

Geisser, et al., "Perception of noxious and innocuous heat stimulation among healthy women and women with fibroymalgia: association with mood, somatic focus, and catastrophizing," *Pain* 102(3):243-50 (Apr. 2003).

Geisser, et al., "The relationship between symptons of post-traumatic stress disorder and pain, affective disturbance and disability among patients with accident and non-accident related pain" *Pain* 66(2-3):207-14 (Aug. 1996).

Giesecke, et al., "Evidence of Augmented Central Pain Processing in Idiopathic Chronic Low Back Pain" *Arthritis & Rheumatism* 50(2):613-623 (Feb. 2004).

Giot et al.; "A Protein Interaction Map of *Drosophila melanogaster*;" *Science*; 2003; vol. 302; pp. 1727-1736.

Golaszewski, et al., "A new pneumatic vibrator for functional magnetic resonance imaging of the human sensorimotor cortex" *Neurosci Lett*. 324(2):125-8 (May 17, 2002).

Golaszewski, et al., "Functional magnetic resonance imaging of the human sensorimotor cortex using a novel vibrotactile stimulator" *Neuroimage* 17(1):421-30 (Sep. 2002).

Gore, et al., "Roentgenographic findings of the cervical spine in asymptomatic people" *Spine* 11(6):521-4 (Jul.-Aug. 1986).

Gorner; "Study Suggests Why Some Feel More Pain;" *Contra Costa Times*; Jul. 29, 2001; pp. A8.

Goubert, et al., "The role of neuroticism, pain catastrophizing and pain-related fear in vigilance to pain: a strutural equations approach" *Pain* 107:234-241 (2004).

Gracely, et al., "Functional Magnetic Resonance Imaging Evidence of Augmented Pain Processing in Fibromyalgia" *Arthritis & Rheumatism* 46(5):1333-1343 (May 2002).

Gracely, et al.; "Is seeing believing? Functional imaging of hysterical anesthesia;" *Neurology*. May 13, 2003;60(9):1410.

Gracely, et al., "Pain catastrophizing and neural responses to pain among persons with fibromyalgia" *Brain* 127:835-843 (2004).

Grachev, et al., "Abnormal brain chemistry in chronic back pain: an in vivo proton magnetic resonance spectroscopy study" *Pain* 89:7-18 (2000).

Grachev, et al.; "Anxiety in healthy humans is associated with orbital frontal chemistry;" *Mol Psychiatry*. Sep. 2000;5(5):482-8; abstract.

Grachev, et al., "Association between dorsolateral prefrontal N-acetyl aspartate and depression in chronic back pain: an in vivo proton magnetic resonance spectroscopy study" *J Neural Transm* 110:287-312 (2003).

Grachev, et al., "Brain chemistry reflects dual states of pain and anxiety in chronic low back pain" *J Neural Transm*. 109(10):1309-34 (Oct. 2002).

Grachev, "Cognitive interference is associated with neuronal marker N-acetyl aspartate in the anterior cingulated cortex: an in vivo $^1$H-MRS study of the Stroop Color-Word task" *Molecular Psychiatry* 6:529-539 (2001).

Grachev, et al., "Cognitive interference sis associated with neuronal marker N-acetyl aspartate in the anterior cingulated cortex: an in vivo (1)H-MRS study of the Stroop Color-Word task" *Mol Psychiatry* 6(5):496, 529-39 (Sep. 2001).

Grachev, et al.; "Decreased levels of N-acetylaspartate in dorsolateral prefrontal cortex in a case of intractable severe sympathetically mediated chronic pain (complex regional pain syndrome, type I); " *Brain Cogn*. Jun. 2002;49(1):102-13; abstract.

Graham, et al., "New devices to deliver samatosensory stimuli during functional MRI" *Magn Reson Med*. 46(3):436-42 (Sep. 2001).

Granges, et al.; "Pressure pain threshold in pain-free subjects, in patients with chronic regional pain syndromes, and in patients with fibromyalgia syndrome;" Arthritis Rheum. May 1993;36(5):642-6; abstract.

Granhag, et al., "Deception detection: interrogators' and observers' decoding of consecutive statements" 135(6):603-20 (Nov. 2001).

Graven-Nielsen, et al.; "Peripheral and central sensitization in musculoskeletal pain disorders: an experimental approach;" *Curr Rheumatol Rep*. Aug. 2002;4(4):313-21; abstract.

Greenough, et al., "The effects of compensation on recovery from low-back injury" *Spine* 14(9):947-55 (Sep. 1989).

Grisart, et al., Conscious and automatic uses of memory in chronic pain patiently *Pain* 94(3):305-13 (Dec. 2001).

Gruber, et al.: "Quantification of Metabolic Differences in the Frontal Brain of Depressive Patients and Controls Obtained by $^1$H-MRS at 3 Tesla;" *Investigative Radiology*; Jul. 2003; pp. 403-408; vol. 38; No. 7.

Guest, et al., "Effect of compensation on emotional state and disability in chronic back pain" *Pain* 48(2) ? ? ? ? (Feb. 1992).

Hadjisstavropoulos, et al., "Subjective judgments of deception in pain expression: accuracy and errors" *Pain* 65(2-3):251-8 (May-Jun. 1996).

Hamdy, et al. "Long-Term Reorganization of Human Motor Cortex Driven by Short-Term Sensory Stimulation;" *Nature Neuroscience*; May 1998; pp. 64-68; vol. 1; No. 1.

Hammonds, et al., "Compensation for work-related injuries and rehabilitation of patients with chronic pain" *South Med J* 71(6):664-5 (Jun. 1978).

Hampton, "Researchers Probe Pathways of Pain—New Insights Emerging From Molecular Studies" *JAMA* vol. 290(18):2391-2 (Nov. 12, 2003).

Herrero, et al., "Wind-up of spinal cord neurons and pain sensation: much ado about something?" *Progress in Neurobiology* 61:169-203 (2000).

Herzberg, et al., "The analgesic effects of R(+)-WIN 55,212-2 mesylate, a high affinity cannabinoid agonist, in a rat model of neuropathic pain" *Neurosci Lett*. 221(2-3):157-60 (Jan. 17, 1997).

Hildebrandt; "Relevance of Nerve Blocks in Treating and Diagnosing Low Back Pain—is the Quality Decisive?;" *Schmerz*; Dec. 2001; pp. 474-483; vol. 15; No. 6; Abstract.

Hofbauer, et al.; "Cortical Representation of the Sensory Dimension of Pain;" *Journal of Neurophysiology*; 2001; pp. 402-411; vol. 86.

Horwitz; "Relating fMRI and PET Signals to Neural Activity by Means of Large-Scale Neural Models;" *Neuroinformatics*; 2004; pp. 251-266; vol. 2; No. 2; Abstract.

Howard, et al.; "Seeing visual hallucinations with functional magnetic resonance imaging;" *Dement Geriatr Cogn Disord*; Mar.-Apr. 1997; pp. 73-77; vol. 8; No. 2; abstract.

Hsieh, et al., "Central representation of chronic ongoing neuropathic pain studied by positron emission tomography" *Pain* 63(2):225-36 (Nov. 1995).

Huppe, et al.; "Chronic widespread pain and tender points in low back pain: a population-based study;" *Z Rheumatol*. Feb. 2004;63(1):76-83; abstract.

Hurwitz, et al., "A randomized trial of medical care with and without physical therapy and chiropractic care with and without physical modalities for patients with low back pain: 6-month follow-up outcomes from the UCLA low back pain study" *Spine* 27(20):2193-204 (Oct. 15, 2002).

Huse, et al.; "Cortical reorganization and pain. Empirical findings and therapeutic implication using the example of phantom pain;" *Schmerz*.: Apr. 2001; pp. 131-137; vol. 15; No. 2; abstract.

Igarashi, et al., "Exogenous Tumor Necrosis Factor-Alpha Mimics Nucleus Pulposus-Induced Neuropathology" *Spine* 25(23):2975-2980 (2000).

Inui, et al.; "Pain processing within the primary somatosensory cortex in humans;" *Eur J Neurosci*. Nov. 2003;18(10):2859-66; abstract.

Ito, et al., "Predictive signs of discogneic lumbar pain on magnetic resonance imaging with discography correlation" *Spine* 23(11):1252-8; discussion 1259-60 (Jun. 1, 1998).

Ivancihev, et al., [Brain somatosensory evoked potentials in myofascial pain syndromes] *Zh Nevrol Psikhiatr Im S S Korsakova* 102(7):32-5 (2002).

Jarvik, et al., "The Longitudinal Assessment of Imaging and Disability of the Back (LAIDBack) Study: baseline data" *Spine* 26(10):1158-66 (May 15, 2001).

Jensen, et al., "Assessing the needs of patients in pain : a matter of opinion?" *Spine* 25(21):2816-23 (Nov. 2000).

Jensen, et al., "Magnetic resonance imaging of the lumbar spine in people without back pain" *N Engl J Med*. 331(2):69-73 (Jul. 14, 1994).

Johanek, et al., "Cannabinoids attenuate capsaicin-evoked hyperalgesia through spinal and peripheral mechanisms" *Pain* 93(3):303-15 (Sep. 2001).

Johnson, Jr. et al., "The contribution of executive processes to deceptive responding" *Neuropsychologia* 42:876-901 (2004).

Joliot, et al.; "FMRI and PET of Self-Paced Finger Movement: Comparison of Intersubject Stereotaxic Averaged Data;" *Neuroimage*; Oct. 1999; pp. 430-447; vol. 10; No. 4; Abstract.

Jones; "Cortical and subcortical contributions to activity-dependent plasticity in primate somatosensory cortex;" *Annu Rev Neurosci*. 2000;23:1-37; abstract.

Kalb; "Taking a New Look at Pain;" *Newsweek*; May 19, 2003; pp. 45-46.

Karas, R. "The relationship between nonorganic signs and centralization of symptoms in the prediction of return to work for patients with low back pain" *Phys Ther* 77(4):354-60; discussion 361-9 (Apr., 1977).

Karppinen, et al., "Magnetic resonance imaging findings in relation to the COL9A2 tryptohan allele among patients with sciatica" *Spine* 27(1):78-83 (Jan. 1, 2002).

Karppinen, et al., "Radiologic phenotypes in lumbar MR imaging for a gene defect in the COL9A3 gene of type IX collagen" *Radiology* 227(1):143-8; Epub Feb. 19, 2003 (Apr. 2003)

Karpinnen, et al.; "Tumor Necrosis Factor-α Monoclonal Antibody, Infliximab, Used to Manage Severe Sciatica;" *Spine*; 2003; pp. 750-754; vol. 28; No. 8.

Kawaguchi, et al., "Association Between an Aggrecan Gene Polymorphism and Lumbar Disc Degeneration" *Spine* 24(23):2456-2460 (1999).

Kayama, et al., "Cultured, autologous nucleus pulposus cells induce functional changes inspinal nerve roots" *Spine* 23(20):2155-8 (Oct. 15, 1998).

Kayama, et al., "Incision of the annulus fibrosus induces nerve root morphologic, vascular, and functional changes. An experimental study" *Spine* 21(22):2539-43 (Nov. 15, 1996).

Kemeny, et al.; "Comparison of Continuous Overt Speech fMRI using BOLD and Arterial Spin Labeling;" *Hum Brain Mapp*; Oct. 14, 2004; pp. 173-183; vol. 24; No. 3; Abstract.

Kerttula, et al., "Post-traumatic findings of the spine after earlier vertebral fracture in young patients: clinical and MRI study" *Spine* 25(9):1104-8 (May 1, 2000).

Khasabov, et al.; "Spinal neurons that possess the subtance P receptor are required for the development of central sensitization;" *J Neurosci*. Oct. 15, 2002;22(20):9086-98.

Kiehl, et al., "Error processing and the rostral anterior cingulated: an event-related fMRI study" *Psychophysiology* 37(2):216-23 (Mar. 2000).

Kilgard, et al.; "Cortical network reorganization guided by sensory input features;" *Biol Cybern*; Dec. 2002; pp. 333-343; vol. 5-6; abstract.

Kinahan, et al.; "A Direct Comparison Between Whole-Brain Pet and Bold fMRI Measurements of Single-Subject Activation Response;" *Neuroimage*; Apr. 1999; pp. 430-439; vol. 9; No. 4; Abstract.

Klekamp, et al., "Results of elective lumbar discectomy for patients involved in the workers' compensation system" *J Spinal Disord*. 11(4):277-82 (Aug. 1998).

Klippel; *Primer on the Rheumatic Diseases*; Nov. 15, 2001; pp. 230, 256-258; twelfth Edition; Arthritis Foundation.

Korhonen, et al., "Efficacy of Infliximab for Disc Herniation-Induced sciatica One-Year Follow-up" *Spine* 29(19):2115-2119 (2004).

Kosek, et al.. "Abnormalities of somatosensory perception in patients with painful osteoarthritis normalize following successful treatment" *Eur J Pain* 4(3):229-38 (2000).

Kramis, et al., "Non-nociceptive aspects of persistent musculoskeletal pain" *J Orthop Sports Phys Ther*. 24(4):255-67 (Oct. 1996).

Kupers, et al., "Positron emission tomography study of a chronic pain patient successfully treated with somatosensory thalmamic stimulation" *Pain* 87(3):295-302 (Sep. 2000).

Kuroda, et al.; "Pain information pathways from the periphery to the cerebral cortex;" *Yakugaku Zasshi*. Jul. 2003;123(7):533-46; abstract.

Langleben, et al., "Brain activity during simulated deception: an event-related functional magnetic resonance study" *Neuroimage* 15(3):727-32 (Mar. 2002).

Lauder, "Musculoskeletal disorders that frequently mimic radiculopathy" *Phys Med Rehabil Clin N Am* 13(3):469-85 (Aug. 2002).

Leavitt, "Organic status, psychological disturbance, and pain report characteristics in low-back-pain patients on compensation" *Spine* 7(4):398-402 (Jul.-Aug. 1982).

Lee, et al., "Lie detection by functional magnetic resonance imaging" *Hum Brain Mapp* 15(3):157-64 (Mar. 2002).

Leffler, et al., "Injection of hypertonic saline into musculus infraspinatus resulted in referred pain and sensory disturbances in the ipsilateral upper arm" *Eur J Pain*. 4(1):73-82 (2000).

Lerner, "Working Wonders" *Medicine Michigan* pp. 32-37 (Fall 2001).

Levander; Sensory sensitization, part I: Mechanisms behind fibromyalgia. "So my wife's pain system has become unnecessarily efficient;" *Lakartidningen*. Apr. 30, 2003;100(18):1608-9, 1612-7; abstract.

Li, et al., "The cannabinoid receptor agonist WIN 55, 212-2 mesylate blocks and the development of hyperalgesia produced by capsaicin in rats" *Pain* 81(1-2):25-33 (May 1999).

Lings, et al., "[Whole body vibrations and low back pain]" *Ugeskr Laeger* 160(29):4298-301 (Jul. 13, 1998).

Liu, et al.; "Activation of spinal N-methyl-D-aspartate or neurokinin receptors induces long-term potentiation of spinal C-fibre-evoked potentials;" *Neuroscience*. Oct. 1998;86(4):1209-16.

Logothetis; "The Neural Basis of the Blood-Oxygen-Level-Dependent Functional Magnetic Resonance Imaging Signal;" *Philos Trans R Soc Lond B Biol Sci*; Aug. 29, 2002; pp. 1003-1037; vol. 357; No. 1424; Abstract.

Lutz, et al., "Looking Back on Back Pain: Trial and Error of Diagnoses in the 20th Century" *Spine* 28(16):1899-1905 (2003).

Lyoo, et al., "Multinuclear magnetic resonance spectroscopy of high-energy phosphate metabolites in human brain following oral supplementation of creatine-monohydrate" *Psychiatry Res*. 123(2):87-100 (Jun. 30, 2003).

MacFarlane, et al., "Employment and physical work activities as predictors of future low back pain" *Spine* 22(10):1143-9 (May 15, 1997).

MacFarlane, et al.; "The natural history of chronic pain in the community: a better prognosis than in the clinic?;" *J. Rheumatol*. Sep. 1996;23(9):1617-20.

Maihöfner, et al., "Cortical processing of brush-evoked aliodynia" *NeuroReport* vol. 14:6 (May 2003).

Mailis, et al.; "Unexplainable nondermatomal somatosensory deficit in patients with chronic nonmalignant pain in the context of litigation/compensation: a role for involvement of central factors?;" *J Rheumatol*; Jun. 2001; pp. 1385-1393; vol. 28; No. 6; abstract.

Mailis-Gagnon, et al.; "Altered central somatosensory processing in chronic pain patients with "hysterical" anesthesia.;" *Neurology*..May 13, 2003;60(9):1501-7.

Malisza, et al., "Functional MRI of the rat lumbar spinal cord involving painful stimulation and the effect of peripheral joint mobilization" *J Magn Reson Imaging*. 18(2):152-9 (Aug. 2003).

Marshall; "Intradiscal Enzyme for Back Pain;" *The Medical Journal of Australia*; Sep. 22, 1973; pp. 616.

Martinez-Bisbal, et al., "Cognitive impairment: classification by 1H magnetic resonance spectroscopy;" *Eur J Neurol*. Mar. 2004;11(3):187-93.

Marx, et al., "Prolonging the Agony" *Science* 305:326-329 (Jul. 16, 2004).

Matsubara, et al., "Serial changes on MRI in lumbar disc herniations treated conservatively" *Neuroradiology* 37(5):378-83 (Jul. 1995).

Matsui, et al., "Familial predisposition for lumbar degenerative disc disease. A case-control study" *Spine* 23(9):1029-34 (May 1, 1998).

Mazza, et al.; "A dynamical model of fast cortical reorganization;" *J Comput Neurosci*.; Mar.-Apr. 2004; pp. 177-201; vol. 16; No. 2; abstract.

McCarron, et al. "The Inflammatory Effect of Nucleus Pulposus. A Possible Element in the Pathogenesis of Low-back Pain" *Spine* 12(8) (1987).

McLain, et al., "Nuclear clefting in dorsal root ganglion neurons: a response to whole body vibration" *J Comp Neurol* 322(4):538-47 (Aug. 22, 1992).

Mendelson, "Chronic Pain, Compensation and Clinical Knowledge" *Theoretical Medicine* 12:227-246 (1991).

Mendelson, "'Compensation neurosis' revisited: outcome studies of the effects of litigation" *J Psychosom Res*. 39(6):695-706 (Aug. 1995).

Mendelson, "Compensation, pain complaints, and psychological disturbance" *Pain* 20(2):169-77 (Oct. 1984).

Michael, et al., "Catastrophizing and pain sensitivity among chronic pain patients: moderating effects of sensory and affect focus," *Ann Behav Med*. 27(3):185-94 (Jun. 2004).

Milette, et al., "Radiating pain to the lower extremities caused by lumbar disk rupture without spinal nerve root involvement" *AJNR Am J Neuroradiol*. 16(8):1605-13; discussion 1614-5 (Sep. 1995).

Miller, et al., "Predictors of 30-month outcome after perinatal depression: role of proton MRS and socioeconomic factors" *Pediatr Res*. 52(1):71-7 (Jul. 2002).

Miyoshi, et al., "Accuracy of the results measured by in vivo 1H-MRS using model solutions" *Tokushima J Exp Med*. 39(1-2):63-7 (Jun. 1992).

Moene, et al.; "Organic syndromes diagnosed as conversion disorder: identification and frequency in a study of 85 patients;" *J Psychosom Res*. Jul. 2000;49(1):7-12; abstract.

Moriwaki, "Topographical features of cutaneous tactile hypoesthetic and hyperesthetic abnormalities in chronic pain" *Pain* 81(1-2):1-6 (May 1999).

Moss; "Relief of Pain By Acupuncture;" *The Lancet*; Aug. 11, 1973; pp. 320.

Mottaghy, et al.; "Comparison of PET and fMRI Activation Patterns During Declarative Memory Processes;" *Nuklearmedizin*; Nov. 2000; pp. 196-203; vol. 39; No. 7; Abstract.

Muller, et al., "The Influence of previous low back trouble, general health, and working conditions on future sick-listing because of low back trouble. A 15-year follow-up study of risk indicators for self-reported sick-listing caused by low back trouble" *Spine* 24(15):1562-70 (Aug. 1, 1999).

Nakata, et al.; "Movements modulate cortical activities evoked by noxious stimulation;" *Pain*, Jan. 2004;107(1-2):91-8; abstract.

Nattrass, et al.; "Lumar Spine Range of Motion as a Measure of Physical and Functional Impairment: an Investigation of Validity;" *Clin Rehabil*; Jun. 1999; pp. 211-218; vol. 13; No. 3; Abstract.

Neylan, et al., "Attention, learning, and memory in posttraumatic stress disorder" *J Trauma Stress* 17(1):41-6 (Feb. 2004).

Nicholson, et al.; "Comorbidities in chronic neuropathic pain;" *Pain Med*. Mar. 2004;5 Suppl 1:S9-S27; abstract.

Nicolelis, et al., "Potential circuit mechanisms underlying concurrent thalamic and cortical plasticity" *Rev Neurosci* 9(3):213-24 (Jul. 1998).

Niemisto, et al.; "Radiofrequency denervation for neck and back pain. A systematic review of randomized controlled trials;" *Spine*; 2003; pp. 1877-1888; vol. 28; No. 16.

Nilsson; "Measuring Passive Ceryical Motion: A Study of Reliability;" *J.Manipulative Physiol Ther*.; Jun. 1995; pp. 293-297; vol. 15; No. 5; Abstract.

Nitschke, et al.; "Reliability of the American Medical Association Guides' Model for Measuring Spinal Range of Motion. Its Implication for Whole-Person Impairment Rating;" *Spine*; Feb. 1, 1999; pp. 262-268; vol. 24; No. 3; Abstract.

Noponen-Hietala, et al.; "Sequence variations in the collagen IX and XI genes are associated with degenerative lumbar spinal stenosis;" *Ann Rheum Dis*. Dec. 2003;62(12):1208-14; abstract.

Nygaard, et al., "The Inflammatory properties of contained and noncontained lumbar disc herniation" *Spine* 22(21):2484-8 (Nov. 1, 1997).

Olmarker, et al.; "Changes in spontaneous behavior in rats exposed to experimental disc herniation are blocked by selective TNF-alpha inhibition;" *Spine*. Aug. 1, 2003;28(15):1635-41; abstract.

Olmarker, et al., "Selective Inhibition of Tumor Necrosis Factor-α Prevents Nucleus Pulposus-Induced Thrombus Formation, Intraneural Edema, and Reduction of Nerve Conductive Velocity" *Spine* 26(8):863-869 (2001).

Olmarker, et al., "The effects of normal, frozen, and hyaluronidase-digested nucleus pulposus on nerve root structure and function" *Spine* 22(5):471-5; discussion 476 (Mar. 1, 1997).

Olmarker, et al., "Tumor Necrosis Factor α and Nucleus-Pulposus-Induced Nerve Root Injury" *Spine* 23(23):2538-2544 (1998).

Olmarker, et al., "Ulatrastructural changes in spinal nerve roots induced by autologous nucleus pulposus" *Spine* 21(4):411-4 (Feb. 15, 1996).

Ombregt, et al.; "Section Once: General Principles, Chapter Two: Pressure On Nerves" *A System of Orthopaedic Medicine*; 2003; pp. 6-22; Second Edition: Churchill Livingstone.

Ombregt, et al.; "Section Once: General Principles, Chapter One: Pain" *A System of Orthopaedic Medicine*; 2003; pp. 28-29; Second Edition; Churchill Livingstone.

Omoigui; "The Biochemical Origin of Pain: How a new law and new drugs have led to a Medical breakthrough in the treatment of Persistent Pain;" 2002-2003; S.O.T.A. Technologies, Inc.

Onda, et al.; "Effects of Neutralizing Antibodies to Tumor Necrosis Factor-Alpha on Nucleus Pulposus-Induced Abnormal Nociresponses in Rat Dorsal Horn Neurons;" *Spine*; 2003; pp. 967-972; vol. 28; No. 10.

O'Neill, et al., "Disc stimulation and patterns of referred pain" *Spine* 27(24):2776-81 (Dec. 15, 2002).

Ostergaard, et al.; "Absolute Cerebral Blood Flow and Blood Volume Measured by Magnetic Resonance Imaging Bolus Tracking: Comparison with Positron Emission Tomography Values;" *J. Cereb Blood Flow Metab*.; Apr. 1998; pp. 425-432; vol. 18; No. 4; Abstract.

Osti, et al., "Annular tears and disc degeneration in the lumbar spine. A post-mortem study of 135 discs" *J Bone Joint Surg Br*. 74(5):678-82 (Sep. 1992).

Osti, et al., "MRI and discography of annular tears and intervertebral disc degeneration. A prospective clinical comparison" *J Bone Joint Surg Br*. 74(3):431-5 (May 1992).

Otani, et al., "Experimental disc herniation: evaluation of the natural course" *Spine* 22(24):2894-9 (Dec. 15, 1997).

Ozawa, et al., "Chronic effects of the nucleus pulposus applied to nerve roots on ectopic firing and conduction velocity" *Spine* 26(24):2661-5 (Dec. 15, 2001).

Paassilta, et al., "Identification of a novel common genetic risk factor for lumbar disk disease" *JAMA* 285(14):1843-9 (Apr. 11, 2001).

Papageorgiou, et al., "Estimating the prevalence of low back pain in the general population. Evidence from the South Manchester Back Pain Survey" *Spine* 20(17):1889-94 (Sep. 1, 1995).

Park, et al., "Cognitive function in fibromyalgia patients" *Arthritis Rheum* 44(9):2125-33 (Sep. 2001).

Park, et al., "Fissuring of the posterior annulus fibrosus in the lumbar spine" *Br J Radiol*. 52(617):382-7 (May 1979).

Park; "Postcards From The Brain;" *Time*; Jan. 20, 2003; 4 pages; vol. 161; No. 3; Time, Inc.

Parks, et al.; "A Comparison of Lumbar Range of Motion and Functional Ability Scores in Patients with Low Back Pain: Assessment for Range of Motion Validity;" *Spine*; Feb. 15, 2003; pp. 380-384; vol. 28; No. 4.

Pattany, et al.; "Proton magnetic resonance spectroscopy of the thalamus in patients with chronic neuropathic pain after spinal cord injury;" *AJNR Am J Neuroradiol*. Jun.-Jul. 2002;23(6):901-5.

Peng, et al.; "Effects of *Ginkgo biloba* extract on acute cerebral ischemia in rats analyzed by magnetic resonance spectroscopy;" *Acta Pharmacol Sin*. May 2003;24(5):467-71.

Peters, et al., "Differences in pain perception and sensory discrimination between chronic low back pain patients and healthy controls" 36(1):47-53 (Jan. 1992).

Petrovic, et al. "A PET activation study of dynamic mechanical allodynia in patients with monoeuropathy;" *Pain*. Dec. 1999;83(3):459-70; abstract.

Petrovic, et al., "Brainstem involvement in the initial response to pain" *Neuroimage* 22:995-1005 (2004).

Petzke, et al.; "Increased pain sensitivity in fibromyalgia: effects of stimulus type and mode of presentation;" *Pain* Oct. 2003;105(3):403-13.

Peyron, et al.; "Functional imaging of brain responses to pain. A review and meta-analysis (2000);" *Neurophysiol Clin*. Oct. 2000;30(5):263-88.

Peyron, et al. "Parietal and cingulate processes in central pain. A combined positron emission tomography (PET) and functional magnetic resonance imaging (fMRI) study of an unusual case;" *Pain*. Jan. 2000;84(1):77-87; abstract.

Pope, et al., "Kappa Delta Award. Low back pain and whole body vibration" *Clin Orthop* (354):241-8 (Sep. 1998).

Pope, et al., "Vibration of the spine and low back pain" *Clin Orthop* (279):49-59 (Jun. 1992).

Porro, et al.; "Functional Activity Mapping of the Mesial Hemispheric Wall during Anticipation of Pain;" *Neuroimage*; Aug. 2003; pp. 1738-1747; vol. 19; No. 4; Abstract.

Porter, et al., "Truth, Lies, and videotape: an investigation of the ability of federal parole officers to detect deception" *Law Hum Behav* 24(6):643-58 (Dec. 2000).

Rabben, et al.; "Prolonged analgesic effect of ketamine, an N-methyl-D-aspartate receptor inhibitor, in patients with chronic pain;" *J Pharmacol Exp Ther*. May 1999;289(2):1060-6.

Rainville, et al., "Exploration of physicians' recommendations for activities in chronic low back pain" *Spine* 25(17):2210-20 (Sep. 1, 2000).

Rainville, et al., "Pain affect encoded in human anterior cingulated but not somatosensory cortex" *Science* 277(5328):968-71 (Aug. 15, 1997).

Rainville, et al., "The effect of compensation involvement on the reporting of pain and disability by patients referred for rehabilitation of chronic low back pain" *Spine* 22(17):2016-24 (Sep. 1, 1997).

Reinges, et al.; "Preoperative Mapping of Cortical Motor Functional: Prospective Comparison of Function Magnetic Resonance Imaging and [15O]-H2O-Positron Emission Tomography In the Same Co-Ordinate System;" *Nucl Med Commun*; Oct. 2004; pp. 987-997; vol. 25; No. 10; Abstract.

Richards, et al., "Exaggerated hearing loss in noise induced hearing loss compensation claims in Victoria" *The Medical Journal of Australia* 163:360-363 (Oct. 2, 1995).

Rogers, et al.; "An Investigation to Dissociate the Analgesic and Anesthetic Properties of Ketamine using Functional Magnetic Resonance Imaging;" *Anesthesiology*; Feb. 2004; pp. 292-301; vol. 100; No. 2; Abstract.

Rolls, et al., "Representations of pleasant and painful touch in the human orbitofrontal and cingulated cortices" *Cereb Cortex*. 13(3):308-17 (Mar. 2003).

Rosomoff, et al., "Do chronic pain patients' perceptions about their preinjury jobs differ as a function of worker compensation and non-worker compensation status?" *Clin J Pain* 11(4):279-86 (Dec. 1995).

Ross, et al.; "Magnetic resonance spectroscopy in cognitive research;" *Brain Res Brain Res Rev*. Mar. 2004;44(2-3):83-102; abstract.

Ruoff, "Depression in the patient with chronic pain" *J Fam Pract* 43(6 Suppl( S25-33; discussion S34 (Dec. 1996).

Saal, "General principles of diagnostic testing as related to painful lumbar spine disorders: a critical appraisal of current diagnostic techniques" *Spine* 27(22):2538-45; discussion 2546 (Nov. 15, 2002).

Saal, et al., "Management of Chronic Discogenic Low Back Pain with a Thermal Intradiscal Catheter" *Spine* 25(3):382-388 (2000).

Sadato, et al.; "Frequency-Dependent Changes of Regional Cerebral Blood Flow During Finger Movements: Functional MRI Compared to PET;" *J Cereb Blood Flow Metab*; Jun. 1997; pp. 670-679; vol. 17; No. 6; Abstract.

Sawamoto, et al.; "Expectation of Pain Enhances Responses to Nonpainful Somatosensory Stimulation in the Anterior Cingulate Cortex and Parietal Operculum/Posterior Insula: an Event-Related Functional Magnetic Resonance Imaging Study;" *J Neurosci*; Oct. 1, 2000; pp. 7438-7445; vol. 20; No. 19.

Schafers, et al.; "Tumor necrosis factor-alpha induces mechanical allodynia after spinal nerve ligation by activation of p38 MAPK in primary sensory neurons;" *J Neurosci*. Apr. 1, 2003;23(7):2517-21.

Schellhas, et al., "Cervical discogenic pain. Prospective correlation of magnetic resonance imaging and discography in asymptomatic subjects and pain sufferers" *Spine* 21(3):300-11; discussion 311-2 (Feb. 1, 1996).

Schnitzler, et al, "Neurophysiology and functional neuroanatomy of pain perception" *J Clin Neurophysiol*. 17(6):592-603 (Nov. 2000).

Seichi, et al.; "Postoperative expansion of intramedullary high-intensity areas on T2-weighted magnetic resonance imaging after cervical laminoplasty;" *Spine*, Jul. 1, 2004;29(13):1478-82.

Seitz, et al.; "Vibratory Stimulation Increases and Decreases the Regional Cerebral Blood Flow and Oxidative Metabolism: a Positron Emission Tomography (PET) Study;" *Acta Neurol Scand*.; Jul. 1992; pp. 60-67; vol. 86; No. 1; Abstract.

Seltzer, et al.. "Tactual sensitivity of chronic pain patients to nonpainful stimuli" *Pain* 27(3):291-5 (Dec. 1986).

Simmons Jr. et al., "Familial predisposition for degenerative disc disease. A case-control study" *Spine* 21(13):1527-9 (Jul. 1, 1996).

Simmons Jr.;. "Painful lumbosacral sensory distribution patterns; embyrogenesis to adulthood" *Orthop Rev* 22(10):1110-8 (Oct. 1993).

Singer, et al.; "Empathy for pain involves the affective but not sensory components of pain;" *Science*. Feb. 20, 2004;303(5661):1157-62.

Skyba, et al., "Joint manipulation reduces hyperalgesia by activation of monoamine receptors but not opioid or GABA receptors in the spinal cord" *Pain* 106(1-2):159-68 (Nov. 2003).

Slipman, et al., "Side of symptomatic annular tear and site of low back pain: is there a correlation?" *Spine* 26(8):E165-9 (Apr. 15, 2001).

Sluka, et al., "Knee joint mobilization reduces secondary mechanical hyperalgesia induced by capsaicin injection into the ankle joint" *Eur J Pain* 5(1):81-7 (2001).

Smith; "Neuropathic Pain: Drug Targets for Current and Future Interventions;" *Drug News Perspect*: Jan.-Feb. 2004 ; pp. 5-17; vol. 17; No. 1.

Solomon et al., "The role of litigation in predicting disability outcomes in chronic pain patients" *Clin J Pain* 7(4):300-4 (Dec. 1991).

Soros, et al. "Functional Reorganization of the Human Primary Somatosensory Cortex After Acute Pain Demonstrated by Magnetoencephalography;" *Neurosci Lett*.; pp. 195-198; vol. 298; No. 3.

Spence, et al., "Behavioural and functional anatomical correlates of deception in humans" *Neuroreport* 12(13):2849-53 (Sep. 17, 2001).

Spinhoven, et al., "Catastrophizing and internal pain control as mediators of outcome in the multidisciplinary treatment of chronic low back pain" *Eur J Pain* 8(3):211-9 (Jun. 2004).

Staud, et al., "Diffuse noxious inhibitory controls (DNIC) attenuate temporal summation of second pain in normal males but not in normal females or fibromyalgia patients" *Pain* 101(1-2):167-74 (Jan. 2003).

Stewart, et al.; "Lost Productive Time and Cost Due to Common Pain Conditions in the US Workforce;" *JAMA*; Nov. 12, 2003; pp. 2443-2454; vol. 290; No. 18.

Strigo, et al.; "Differentiation of Visceral and Cutaneous Pain in the Human Brain;" *J Neurophysiol*; Jun. 2003; pp. 3294-3303; vol. 89; No. 6.

Stroman, et al., "Functional magnetic resonance imaging at 0.2 Tesla;" *Neuroimage*; 2003; vol. 20; pp. 1210-1214.

Stroman, et al., "Noinvasive assessment of the injured human spinal cord by means of functional magnetic resonance imaging" *Spinal Cord*. 42(2):59-66 (Feb. 2004).

Sullivan, et al. "The Relationship of Lumbar Flexion to Disability in Patients with Low Back Pain;" *Phys Ther*.; Mar. 2000; pp. 240-250; vol. 80; No. 3; Abstract.

Suter, "Employment and litigation: improved by work, assisted by verdict" *Pain* 100(3):249-57 (Dec. 2002).

Suzuki, et al.; "ReN-1869 [(R)-1-(3-(10,11-dihyro-5H-dibenzo[a,d]cyclohepten-5-ylidene)-1-propyl)-3-piperidine carboxylic acid], a novel histamine H1 receptor antagonist, produces potent and selective antinociceptive effects on dorsal horn neurons after inflammation and neuropathy;" *J Pharmacol Exp Ther*. Jun. 2004;309(3):1230-8. Epub Feb. 26, 2004.

Svensson, et al.; "Cerebral Processing of Acute Skin and Muscle Pain in Humans;" *Journal of Neurophysiology*; 1997; pp. 450-460; vol. 78; abstract.

Szpalski, et al. *Lumbar Segmental Instability*; Nov. 1998; 336 pages; Lippincott Williams & Wilkins.

Tagamets, et al.; Interpreting PET and fMRI Measures of Functional Neural Activity: The Effects of Synaptic Inhibition on Cortical Activation in Human Imaging Studies; *Brain Res Bull*; Feb. 2001; pp. 267-273; vol. 54; No. 3; Abstract.

Tait, et al., "Compensation status and symptoms reported by patients with chronic pain" *Arch Phys Med Rehabil* 69(12):1027-9 (Dec. 1988).

Takebayashi, et al., "Effect of nucleus pulposus on the neural activity of dorsal root ganglion" *Spine* 26(8):940-5 (Apr. 15, 2001).

Talairach, et al; Co-Planar Stereotaxic Atlas of the Human Brain: 3-Dimensional Proportional System: An Approach to Cerebral Imaging; 1988; 122 pages; Thieme Medical Publishers.

Tempel, et al.; "Vibration-induced Regional Cerebral Blood Flow Responses in Normal Aging;" *J. Cereb Blood Flow Metab*.; Jul. 1992; pp. 554-561; vol. 12; No. 4; Abstract.

Teresi, et al., "Asymptomatic degenerative disk disease and spondytosis of the cervical spine: MR imaging" *Radiology* 164(1):83-8 (Jul. 1987).

Thernstrom, "Pain, the Disease" *New York Times* (Dec. 16, 2001).

Thomas, et al., "Predicting who develops chronic low back pain in primary care: a prospective study" *BMJ* 318(7199):1662-7 (Jun. 19, 1999).

Throckmorton, et al., "The Impact of Adjacent Level Disc Degeneration on Health Status Outcomes Following Lumbar Fusion" *Spine* 28(22):2546-2550 (2003).

Tobinick, et al., "Perispinal TNF-alpha inhibition for discongenic pain" *Swiss Med Wkly* 133:170-177 (2003).

Tobinick, "Targeted Etanercept for Discogenic Neck Pain: Uncontrolled, Open-Label Results In Two Adults" *Clin Ther*. 25:1211-1218 (2003).

Torquati, et al.; ""Gating" effects of simultaneous peripheral electrical stimulations on human secondary somatosensory cortex: a whole-head MEG study;" *Neuroimage*. Nov. 2003;20(3):1704-13: abstract.

Tracy, et al., "Noxious hot and cold stimulation produce common patterns of brain activation in humans: a functional magnetic resonance imaging study" *Neurosci Lett*. 288(2):159-62 (Jul. 14, 2000).

Turner, et al., "Catastrophizing is associated with pain intensity, psychological distress, and pain-related disability among individuals with chronic pain after spinal cord injury," *Pain*, 98(1-2):127-34 (Jul. 2002).

Urban, et al.; "Central mechanisms in pain;" *Med Clin North Am*. May 1999;83(3):585-96.

Ushida, et al.; "Analgesic Effects of Ketamine Ointment in Patients with Complex Regional Pain Syndrome Type 1;" *Reg Anesth Pain Med*; Sep.-Oct. 2002; pp. 524-528; vol. 27; No. 5; Abstract.

Van Den Hoogen, et al., "The prognosis of low back pain in general practice" *Spine* 22(13):1515-21 (Jul. 1, 1997).

Vanharanta, et al., "Vibration Pain Provocation Can Improve the Specificity of MRI in the Diagnosis of Symptomatic Lumbar Disc Rupture [Article]" *Clinical Journal of Pain* 14(3):239-247 (Sep. 1998).

Vitzthum, et al., "Dynamic examination of the lumbar spine by using vertical, open magnetic resonance imaging" *J Neurosurg*. 93(1 Suppl):58-64 (Jul. 2000).

Vythilingam, et al.; "Focal and lateralized subcortical abnormalities in unipolar major depressive disorder: an automated multivoxel proton magnetic resonance spectroscopy study;" *Biol Psychiatry*.Oct. 1, 2003;54(7):744-50.

Wager, et al.; "Placebo-Induced Changes in FMRI in the Anticipation and Experience of Pain;" *Science*; Feb. 20, 2004; pp. 1162-1167; vol. 303; No. 5661.

Wagner, et al., "Endoneurial Injection of TNF-alpha produces neuropathic pain behaviors" *Neuroreport* 7(18):2897-901 (Nov. 25, 1996).

Waldman, et al.; "The relationship between cognitive impairment and in vivo metabolite ratios in patients with clinical Alzheimer's disease and vascular dementia: a proton magnetic resonance spectroscopy study;" *Neuradiology*. Aug. 2003;45(8):507-12. Epub Jul. 22, 2003; abstract.

Wall, et al.; "Human Brain Plasticity: An Emerging View of the Multiple Substrates and Mechanisms that Cause Cortical Changes and Related Sensory Dysfunctions After Injuries of Sensory Inputs From the Body;" *Brain Res Brain Res Rev*; Sep. 2002; pp. 181-215; vol. 39, No. 2-3.

Wall, "Neurophysiological mechanisms of referred pain and hyperalgesia" *New Trends in Referred Pain and Hyperalgesia* 7(1)2-12 (1993).

Warfield, et al.; *Manual of Pain Mangement*; Jan. 15, 2002; 207 pages; Second Edition; Lippincott Williams & Wilkins.

Wasserman, "Vibration exposure and prevention in the United States" *Nagoya J Med Sci* 57 Suppl:211-8 (May 1994).

Waxman, et al., "A prospective follow-up study of low back pain in the community" *Spine* 25(16):2085-90 (Aug. 15, 2000).

Webster, et al., "Outcomes of Worker's Compensation Claimants With Low Back Pain Undergoing Intradiscal Electrothermal Therapy" *Spine* 29(4):435-441 (2004).

Weich, et al., "Neuroimaging of chronic pain: phantom limb and musculoskeletal pain" *Scand J Rheumatol* 29 Suppl 113:13-8 (2000).

Weintraub, "Chronic pain in litigation. What is the relationship?" *Neurol Clin* 13(2):341-9 (May 1995).

Weiss, et al.; "Cognitive impairment: assessment with brain magnetic resonance imaging and proton magnetic resonance spectroscopy;" J Clin Psychiatry. Mar. 2003;64(3):235-42.

Wiesel, et al., "A study of computer-assisted tomograpy. I. The incidence of positive CAT scans in an asymptomatic group of patients" *Spine* 9(6):549-51 (Sep. 1984).

Wilder, "The Biomechanics of vibration and low back pain" *Am J Ind Med* 23(4):577-88 (Apr. 1993).

Williams, et al.; "Reliability of the Modified-Modified Schober and Double Inclinometer Methods for Measuring Lumbar Flexion and Extension;" *Phys Ther.*; Jan. 1993; pp. 33-44; vol. 73; No. 1; Abstract.

Wilmink, "MR imaging of the spine: trauma and degenerative disease" *Eur Radiol.* 9(7):1259-66 (1999).

Wilson, et al., "Major Depression and Insomnia in Chronic Pain" *The Clinical Journal of Pain* 18:77-83 (2002).

Witting, et al.; "Differential recruitment of endogenous pain inhibitory systems in neuropathic pain patients;" *Pain.* May 2003;103(1-2):75-81; abstract.

Witting, et al.; "Experimental brush-evoked allodynia activated posterior parietal cortex;" *Neurology.* Nov. 27, 2001;57(10):1817-24.

Wolfe: "The relation between tender points and fibromyalgia symptom variables: evidence that fibromyalgia is not a discrete disorder in the clinic;" Ann Rheum Dis. Apr. 1997;56(4):268-71.

Xu, et al., "Work environment and low back pain: the influence of occupational activities" *Occup Environ Med* 54(10):741-5 (Oct. 1997).

Yabuki, et al., "Application of nucleus pulposus to the nerve root simultaneously reduces blood flow in dorsal root ganglion and corresponding hindpaw in the rat" *Spine* 25(12):1471-6 (Jun. 15, 2000).

Yabuki, et al., "Prevention of Compartment Syndrome in Dorsal Root Ganglia Caused by Exposure to Nucleus Pulposus" *Spine* 26(8):870-875 (Apr. 15, 2001).

Yamasaki, et al; "Effects of distraction on pain perception: magneto- and electro-encephalographic studies;" *Brain Res Cogn Brain Res.* May 1999;8(1):73-6; abstract.

Yamasaki, et al.; Effects of distraction on pain-related somatosensory evoked magnetic fields and potential following painful electrical stimulation; *Brain Res Cogn Brain Res.* Mar. 2000;9(2):165-75; abstract.

Yang, et al.; "Noninvasive Detection of Cerebral Plasticity in Adult Human Somatosensory Cortex;" *Neuroreport*; Feb. 24, 1994; pp. 701-704; vol. 5; No. 6; abstract.

Yonekura; "Recent Advances in Functional Neuroimaging;" *Nippon Yakurigaku Zasshi.*; Oct. 1999; pp. 6P-10P; vol. 114; Suppl. 1; Abstract.

Yrjama, et al., "Bony vibration stimulation test combined with magnetic resonance imaging. Can discography be replaced?" *Spine* 22(7):808-13 (Apr. 1, 1997).

Yrjama, et al., "Bony vibration stimulation: a new, non-invasive method for exaiming intradiscal pain" *Eur Spine J* 3(4):233-5 (1994).

Yrjama, et al., "Ultrasonic imaging of lumbar discs combined with vibration pain provocation compared with discography in the diagnosis of internal anular fissures of the lumbar spine" *Spine* 21(5):571-5 (Mar. 1996).

Zaini, et al.; "Comparison of Matched BOLD and FAIR 4.OT-fMRI with [15O]water PET Brain Volumes:" *Med Phys.*; Aug. 1999; pp. 1559-1567; vol. 26; No. 8; Abstract.

Zuberbier, et al.; "Commentary on the American Medical Association Guides' Lumbar Impairment Validity Checks;" *Spine*; Dec. 15, 2001; pp. 2735-2737; vol. 26; No. 24; Abstract.

Zubieta, et al.; "COMT val158met genotype affects mu-opioid neurotransmitter responses to a pain stressor;" Science. Feb. 21, 2003;299(5610):1240-3; abstract.

Zubieta, et al., "Regional mu opioid receptor regulation of sensory and affective dimensions of pain" *Science* 293(5528):311-5 (Jul. 13, 2001).

Zubieta, et al.; "Regulation of Human Affective Responses by Anterior Cingulate and Limbic Mu-Opioid Neurotransmission;" *Arch Gen Psychiatry*; Nov. 2003; pp. 1145-1153; vol. 60; No. 11; Abstract.

Zusman, "Forebrain-mediated sensitization of central pain pathways; 'non-specific' pain and a new image for MT" *Man Ther.* 7(2):80-8 (May 2002).

Zusman; "Forebrain-mediated sensitization of central pathways: 'non-specific' pain and a new image for MT;" Man Ther. May 2002;7(2):80-8; abstract.

Web page; "BrainMap Database;" at URL=http://ric.uthscsa.edu/projects/brainmapdatabase.html; printed Apr. 22, 2005; 2 pages.

Web page; "BrainMap;" at URL=http://ric.uthscsa.edu/projects/brainmap.html; printed Apr. 22, 2005; 1 page.

Web page; Burger; "Thirty-five Percent of People Surveyed Think It's OK to Inflate Insurance Claims;" at URL=www.ircweb.org/news/newsreleases/2000-06-06.htm; printed Feb. 7, 2004; 1 page.

Web page; Maudsley, et al.; "All About Functional Magnetic Resonance Imaging (FMRI);" *Functional MRI*; at URL=http://www.cmrr.drad.umn.edu/fmri.html; printed Jun. 22, 2002; 1 page.

Web page; Meier, et al.; "Division Biophysics (MRI/MRS): Magnetic Resonance Imaging and Spectroscopy;" *Brain Imaging and Spectroscopy; Projects*; at URL=http://www.mir.ethz.ch/brain/brain_proj.html; printed Mar. 5, 2004; 6 pages.

Web page; Parry et al.; "Functional Magnetic Resonance Imaging (fMRI): A "window" into the brain;" at URL=http://www.fmrib.ox.ac.uk/fmri intro/fmri intro.htm; printed Jun. 22, 2004; 9 pages.

Web page; Smith; "Brief Introduction to FMRI;" *Introduction to FMRI*: at URL=http://www.fmrib.ox.ac.uk/fmri intro/brief.html; printed Jun. 22, 2002; 1 page.

Web page; Sylvester; "ACR: Lower-Back and Fibromyalgia Pain Linked, Possible Source Identified;" *Doctor's Guide Personal Edition*; at URL=http://www.docguide.com/news/content.nsf/New.../8525697700573E1885256C600077970; printed Nov. 11, 2002; 1 page.

"Improved, Dynamic fMRI for Monitoring Pain," ©2002, University of California, San Diego, http://invent.ucsd.edu/technology/cases/2006/SD2006-078.htm.

U.S. Appl. No. 60/737,983, filed Nov. 17, 2005, Leung.

* cited by examiner

OBJECTIVE DETERMINATION OF CHRONIC PAIN IN PATIENTS

BACKGROUND OF THE INVENTION

This application relates to a method for objectively determining chronic pain in individuals.

Humans (as well as animals) suffer from two types of pain. Transitory pain, caused by external factors such as impacts, heat, etc. and injuries to tissue caused thereby, or by certain illnesses, can last for short moments to longer periods of time. It typically lasts until the effect on the person's tissue from injury or illness subsides, e.g. until a wound or burn, for example, has partially or fully healed. Humans also suffer long-term or chronic pain, which may or may not be the result of external factors and which typically persists for indeterminate lengths of time. Chronic pain can be debilitating and can prevent the person suffering such pain from leading a normal life, pursuing an occupation, performing many routine activities, and the like. Persons suffering chronic pain are often entitled to compensation from an insurance company, an employer, the government, individuals who negligently or intentionally inflicted the pain, etc. In the past, it was most difficult if not impossible to objectively determine the chronic pain allegedly suffered by a person. Making this determination, however, is important in order to fairly and adequately compensate the pain sufferer.

The root for the problem of objectively determining the presence of chronic pain and/or to quantify it is that pain is perceived by the brain, and there are presently no feasible tests or procedures which can objectively determine if chronic pain is present and, if so, the magnitude thereof. As a result, persons, such as physicians, psychologists, technicians and the like, had to principally rely on a subjective evaluation of the chronic pain by the patient. This is a difficult and highly inaccurate task, leading to unreliable results.

An individual's perception of chronic pain may be incorrect due to a variety of factors, such as his/her mental and/or emotional state, an objectively incorrect perception of the pain by the individual's brain, variations in pain tolerances by individuals, etc.

In addition, the pain sufferer may be motivated to embellish or diminish the chronic pain for purposes unrelated to the pain itself. Thus, an individual might exaggerate, embellish or completely fabricate the presence, description and/or magnitude of chronic pain. Most often this occurs when an individual seeks to be compensated by a third party for the chronic pain he asserts to suffer. The individual may exaggerate or fabricate the chronic pain because he believes this may yield a higher payment from an insurance company, may lead to a higher settlement of a dispute, may assist the individual in prosecuting a lawsuit, may gain sympathy from others, and the like. Individuals also might minimize the chronic pain suffered by them, for example, in order to qualify for a position he/she seeks where chronic pain might be an obstacle.

The processing of insurance claims for compensation as a result of debilitating chronic pain is probably the most frequent occurrence requiring a determination of the presence and/or magnitude of chronic pain. Such claims may be for a one-time lump sum compensation, or for lifelong support as a result of actual, embellished or entirely fabricated assertions of high levels of chronic pain and the disabilities that can flow from them. Since a significant segment of the population suffers from chronic pain, the liabilities incurred by insurance companies and others obligated to compensate the sufferers are very large and typically lie in the billions of dollars per year nationwide.

Persons seeking compensation who do not suffer chronic pain, or suffer it at a non-debilitating level, would, if the claim is accepted, receive unfair compensation to which they are not entitled. This in turn burdens insurance companies and those insured by the insurance companies, because excessive or fraudulent claims lead to higher insurance premiums.

Up to now it has not been feasible to objectively determine the presence and/or amount of chronic pain, in an objective and reliable manner that is comparable, for example, to the way in which the cholesterol level in a patient can be determined with a simple blood test. Instead, claims for compensation due to chronic pain were in the past processed by persons who had experience in such matters. They looked at a variety of factors which can suggest the presence or absence and/or the level of chronic pain based on the patient's current behavior, background, personal and medical history, possible motivations for embellishing or fabricating their description of the chronic pain suffered by them, etc. Although such evaluations of claims are helpful, in that at least gross misstatements, exaggerations and outright untruths by the patient can sometimes be observed or detected, they are, at best, nonscientific, subjective and quite unreliable. As a result, a patient who suffers chronic pain might be wrongly judged as not having it, while another person who cleverly postures might be found to suffer such pain and be unjustifiably compensated.

It is well known that the presence of chronic pain is perceived and established in the brain. It has been suggested to more objectively determine the presence and/or level of chronic pain by observing brain activities that might evidence the presence of chronic pain and/or the level of such chronic pain.

U.S. Pat. No. 6,018,675 (Apkarian), for example, discloses to measure pain in a patient by applying a variable intensity pain stimulus in a time-dependent manner during which the patient's brain responses are recorded using imaging (for example, a functional MR) while the patient indicates the level of discomfort using a perceptometer or other similar pain rating device operated by the patient as the pain stimulus is applied and varied. The pain rating is correlated with the imaging results using a quantitative analysis to characterize the brain's representation of this pain. Color overlays are generated on high resolution anatomical images (MR or other modality) of the brain summarizing the calculated pain-related analysis information.

The Apkarian patent states that, during an examination, the patient is subjected to variable pain over a period of time during which brain responses of the patient are objectively imaged and during which time subjective indications of the level of discomfort of the patient are recorded. Thereafter, the subjective indications of the level of discomfort are correlated with the objectively imaged brain responses in order to characterize the brain's representation of the pain in relation to the patient's perception and irrespective of the details of the stimulus, which may be only weakly related to the perception. In this method, the patient may be externally manipulated in order to inflict a variable pain. Such manipulation may include the movement of a leg in the case of a patient experiencing chronic back pain. In other cases, the variable pain may be provided by the application of an external stimulus such as a thermal stimulus. In all cases, the stimulus perturbs the patient's pain perception and the patient himself/herself provides the perception signal used for analyzing the brain images.

The patient's subjective indications of pain are compared to the brain activities of a group of persons to whom the same pain stimuli were applied. Thus, the Apkarian patent further states that a large number of persons having the same pain-causing condition are tested using the above techniques in order to obtain an "aggregate" value for the condition. This sampling may also include persons who do not have the pain condition to test the reliability of the results obtained. For example, in order to establish an "aggregate" value of the brain images to be expected for a person having a lower back pain condition, several persons are tested to obtain brain images for different levels of pain inflicted on them, for example by raising a person's leg to different angles to the horizontal. That is to say, with a person placed in a supine position, each leg of the person can be raised to different angles to the horizontal, for example in 5° increments. The brain images which are taken for each angular increment are then correlated with the pain rating indicated by that person. The resultant brain images relative to an indicated pain level may then be aggregated for these persons in order to establish an "aggregate" value to be expected for different levels of pain indicated by the rating device.

Once the "aggregate" value has been established, a patient may be subjected to a similar protocol to obtain his/her rating of pain for each angular increment of the leg relative to the horizontal. The brain image of the patient corresponding to the pain rating can then be compared to the aggregate brain image to be expected for the given pain rating. Deviations of the actual brain image from the expected aggregate brain image can then be used as objective evidence of feigned pain.

Thus, the Apkarian patent discloses a method of measuring brain activity in response to a number of pain stimuli successively applied to the patient. Although this approach may be helpful in discerning the pain generated by a number of pain stimuli, the method taught in the Apkarian patent does not and cannot distinguish between chronic pain and transitory pain and cannot establish the presence and/or magnitude of chronic pain on an objective basis.

As a result, these past attempts have not been adopted because of their questionable reliability, accuracy and/or practicability. Thus, there exists a need for a method to objectively determine chronic pain and chronic pain levels with a high degree of accuracy and reliability.

SUMMARY OF THE INVENTION

Sophisticated image scanning techniques are able to detect and quantify neuron activity in the brain. The present invention takes advantage of the discoveries that certain neuron activities which occur in the brain are related to pain sensations received by the brain, and that the pain-related neuron activity in the brain differs between patients suffering chronic pain and persons without chronic pain. In accordance with the present invention, this difference is advantageously used to detect whether a person suffers chronic pain on a purely objective basis without requiring any input from the patient being examined. As a result, the patient cannot consciously influence the process and the ultimate determination whether he/she suffers chronic pain.

Pain occurring in a patient's body sends pain impulses to the brain, where they are initially processed at the prefrontal area of the brain, including the cortical and subcortical portions thereof. Such pain impulses cause neuron activity in the prefrontal area of the brain, which can be observed on functional magnetic resonance images ("f-MRI"). Thus, the application of a pain stimulus, such as vibration, pressure or heat, to any part of the patient's body can be observed by increased neuron activity in the brain, at least initially principally in the prefrontal area thereof. However, the observable neuron activity in response to an applied pain stimulus differs between patients who suffer chronic pain and persons who are free of such pain. Specifically, the chronic pain sufferer is much more sensitive to the applied pain stimulus than a person free of chronic pain, which shows up on the f-MRI as increased neuron activity in the brain as compared to the f-MRI of a person free of chronic pain to whom the same pain stimulus was applied.

Moreover, in a chronic pain sufferer, the observed brain activity in response to a given pain stimulus is a function of the amount of chronic pain that is present. Thus, the level of neuron activity in the brain bears a direct relationship to the amount of chronic pain suffered by the patient. This then provides a quantitative determination of the level of chronic pain the patient suffers.

To make the comparison between the neuron activity caused by a pain stimulus in a patient suffering chronic pain and in persons free of such pain, the patient's brain activity, as shown in his brain f-MRI, is compared to a standardized f-MRI that is assembled from brain activities in a representative sample of pain-free persons (control group) to whom the same pain stimulus was applied.

In its broadest form, the present invention involves applying a pain stimulus to the patient claiming to suffer chronic pain, observing changes in the brain caused by the stimulus, and comparing the observed brain changes to brain changes caused by the same stimulus applied to a group of persons who are free of chronic pain. An evaluator, such as a physician, for example, then judges if the differences between the observed brain changes in the patient and in the control group are statistically significant. If they are, the comparison results in an objective determination that the patient suffers from chronic pain. In addition, the comparison of the quantitative changes to the brains of the patient and of the control group allows one to determine the level of chronic pain suffered by the patient with a high degree of objective accuracy.

In practical terms, the present invention involves initially preparing a library of standard f-MRIs for different control groups consisting of persons who are free of chronic pain. Standard f-MRIs are typically prepared by subjecting each member of the control group to the same pain stimulus while taking f-MRIs of the brain activity caused by the pain stimulus. All f-MRIs of the members of the control group are then statistically combined into the standard f-MRI for a given pain stimulus and for a control group the members of which have predetermined characteristics, as is further discussed below.

The patient claiming to suffer chronic pain is tested by applying the same pain stimulus to him/her as was applied to the members of the control group and taking an f-MRI of his/her brain activity. An evaluator then compares the patient's f-MRI to the standard f-MRI. If the patient's f-MRI shows a statistically significantly higher brain activity than is the case for the standard f-MRI, the patient is judged to suffer chronic pain. What is statistically significant can to some extent be left to the judgment but can at all times be objectively controlled, for example by defining that a standard deviation of 1 to 1½ from the mean of the standard, bell-shaped distribution of observed emissions is presently proposed, particularly for processing insurance claims as further discussed below.

Preferably, the process is computerized and automated so that the computer will provide an output which numerically (or otherwise, e.g. in graphic form) reflects the quantitative and qualitative differences between the patient's f-MRI and the standard f-MRI. In this manner, the process can be freed of most subjective inputs in determining the presence of chronic pain, including subjective inputs from an evaluator, by predefining computer output levels which indicate the presence of chronic pain.

The present invention is useful whenever the presence of chronic pain in a patient needs to be verified. The invention has particular applicability to the evaluation of insurance or other compensation claims based on chronic pain that may render the patient partially or wholly unable to perform certain tasks, hold jobs, and the like. A fairly substantial segment of the population suffers from chronic pain and makes claims for compensation. Unlike the past, when chronic pain could only be verified empirically and based on the evaluator's observations, including subjective input provided by the patient, which is quite inaccurate, most difficult if not impossible to verify, and is subject to errors that might deny compensation to a person entitled to it, while unfairly awarding it to another person who does not suffer chronic pain, the present invention provides a completely objective determination of whether chronic pain is present in a manner that cannot be influenced by the patient.

Thus, another aspect of the invention provides a method for processing insurance claims by alleged sufferers of chronic pain which involves measuring the brain activity in the patient caused by a pain stimulus applied to his/her body and comparing the patient's brain activities to the brain activities of persons to whom the same stimulus was applied but who are free of chronic pain. If the comparison shows there is a statistically significant difference, the patient is judged to suffer chronic pain, and this information is then forwarded to the insurance company (or other entity against whom the patient made a claim for compensation) for further processing, such as determining whether the patient is entitled to compensation.

The present invention is particularly useful for processing insurance and other claims for compensation by chronic pain sufferers. The invention takes away the possibility for a patient to embellish, enhance or even entirely fabricate the presence of chronic pain, a tendency that has been observed to apply to as many as 40% of insurance claimants. Thus, insurance claims processed in accordance with the present invention will have a very high degree of accuracy, thereby ensuring that chronic pain sufferers are adequately compensated while preventing unscrupulous persons from effectively defrauding the insurance system by making inaccurate or outright false assertions, which, in the past, could not be readily verified.

Responses of the Brain to Pain

The human brain is not static, and with ongoing or chronic pain there is an adaptive reorganization of the brain. This has been observed on f-MRIs, MRSs (magnetic resonance spectrometer), PET-scans, MEGs (magnetoencephalography), etc. Scientific studies have shown that, with pain, there is brain plasticity and because of the brain plasticity there are changes in areas of the brain. For example, in the somatosensory map (how the body looks at itself), there is sensory reorganization, there is prefrontal cortical hyperactivity, there are changes in the brain neurotransmitter levels, and there are changes in pain-related neuron activity involving secondary pain and especially chronic pain.

Careful physical examinations have shown a relationship between, for example, patients with a low tender point count, and as the pain becomes more severe, the clinical examination will change with an increase in the positive tender point count, allodynia (non-nociceptive stimulation which is painful) changes in the somatosensory map, etc. Even absent the scientific studies, careful clinical examinations demonstrate that there is plasticity in the central nervous system. Studies have also shown that with the healing or disappearance of the pain generator and a resulting decrease or absence of chronic pain, the nervous system will return to normal.

Clinical observation and/or examination of the patient may present confusing and variable findings to the unknowledgeable evaluator/physician. For example, in hysterical conversion reactions, individuals with chronic pain will exhibit non-anatomic and non-physiologic patterns of pain. With an f-MRI, these changes become explainable because they involve changes in the somatosensory map, or how the body looks at itself. These brain and neuro pattern changes are observable on f-MRIs.

Conventional MRIs allow imaging of both soft and hard tissue anatomy. Water is slightly magnetic in a high magnetic field. Some of the protons in the water line up and become a molecular compass. A radiofrequency ("RF") signal sent through the human body in a strong magnetic field will, depending on the amount of water/protons in the tissue, allow obtaining a cross-sectional image. The resultant image is based on the amount of water in the tissue. Bone, ligaments, muscle, etc. can be imaged. MRIs using this technique give a detailed cross-sectional image of the soft tissue which is impossible with x-rays.

F-MRIs go further and allow an indirect observation of neuron activation. The neural activation image production comes from the oxygen in the blood. The hemoglobin of blood contains iron, which can combine with oxygen carried by the blood. In brain tissue, the hemoglobin gives up its oxygen, which changes the magnetic properties of the hemoglobin. The change in the magnetic property of the hemoglobin results in a disturbance in the local magnetic field. Magnetized water molecules close to the hemoglobin oxygen exchange lose their magnetic orientation for a few nanoseconds, after which they will recover. RF signals beamed through the brain tissue pick up these magnetic alterations, which can be seen on the f-MRI, thereby identifying the changes that take place in the brain. Computers with appropriate software such as the AFNI (*Analysis of Functional Neuro Imaging* by Robert Cox Ph.D.; Bio-research Institute, Medical College of Wisconsin and now at the National Institute of Health) are used to create maps of the location of the neural activation, and its strength, for example as a percentage of the neurons becoming active, and/or as a change of the pattern of the neuron activation.

More specifically, the intense magnetic field of the f-MRI allows a sufficient number of the water molecules (which are only slightly magnetic) to line up magnetically to permit depended level technique ("BOLD") to become effective. The BOLD technique takes advantage of the fact there are changes in the blood during nutrition of the neuron cells for activation. The hemoglobin will go from a diamagnetic oxyhemoglobin to paramagnetic deoxyhemoglobin. Change in the hemoglobin, in the red blood cell, from diamagnetic to paramagnetic results in a change in the magnetic signature of the molecule. The magnetic signature changes lead to a disturbance of the local magnetic field surrounding the hemoglobin. The magnetized water molecules, because of the disturbance in the local magnetic field, will lose their magnetic orientation. However, after the local magnetic signal change stabilizes, the molecules will again align themselves with the strong external magnetic field, and when the realignment occurs, there is a generation of RF signals. The realignment RF signal can be detected and the changes in the magnetic field recorded on the f-MRI.

In other words, with activation of the neurons by stimulation, there is a requirement for oxygen to complete the chemical reactions necessary for brain/neuron metabolism. This metabolic requirement occurs when the neuron is stimulated and then becomes metabolically active. The metabolism requires oxygen, and there is passage of the oxygen from the hemoglobin, or blood, to the neuron. This involves a momentary loss of magnetic orientation, which generates RF signals and becomes visible on the f-MRI scan. Magnetic changes can be mapped showing location of the activation, the magnitude thereof, the percentage of neurons becoming active, and the pattern of neuron activation that becomes visible on the f-MRI.

Thus, input to the brain from the body caused by sensory dysfunction or pain results in changes in the brain responses. These changes include neurochemical changes/molecular changes and the functional alterations of normal excitement and inhabitation of neurotransmissions. There are also new neural connections made and a reorganization, or makeover, of the somatosensory section of the brain. These changes are modulated by nociceptive or pain input. The changes are essentially hyper-responsiveness associated with reorganization.

Research has been carried out to identify pain generators in the back. This has shown that back pain can be due to injuries to back muscles, intraspinous ligaments, the dura matter, the sacroiliac joint, etc. All these can be pain generators. Studies have shown 41% of back pain is secondary to discogenic disease, 34.4% is secondary to sacroiliac joint pain, and 18% originates from the zygapophyseal joint.

One of the major pain generators in the spine is "tumor necrosis factor alpha" from a pain-generating disc of the spinal cord. After approximately the age of 20 there is a decreased blood supply to the human intervertebral disc. This results in "apoptosis", which is a non-necrotic or programmed death of the cell. A by-product of the cell breakdown is "tumor necrosis factor alpha".

Leaking of "tumor necrosis factor alpha" through rents or tears in the annulus fibrosis, which holds the disc nucleus pulposus in place, causes a chemical irritation of the spinal nerve root and its investments. X-rays, MRIs, electrodiagnostic studies, physical examination, etc. will frequently demonstrate no pathology. Discograms will be positive and MRI gadolinium studies will also show positive results. Vibratory testing will also cause significant increase in pain.

With chronic pain there are associated chemical changes in the brain. There is a decrease in N-acetyl aspartate and changes in other brain metabolites. The chemical changes will result in depression, anxiety and/or a loss of cognitive memory functions. The pain and discomfort, coupled with depression, can become so severe that, on occasion, chronic pain/ongoing pain individuals will commit suicide.

Chronic pain also involves changes in somatosensory cortical inhibition of the pain perceived and changes in reflexes, as well as changes in the excitability, for example in the motor cortex. The somatosensory maps of individuals with chronic pain show changes in perception of the body by the brain, which do not occur in persons without chronic pain.

A central feature made use of by the present invention is the difference in which transitory pain or a "pain stimulus" temporarily applied to a patient leads to different brain activities, or changes in brain activity, depending on whether the person has chronic pain. Changes in the brain due to brain plasticity, new neurons growing, as well as inhibition or augmentation of other pain pathways which are secondary to changes in the neurotransmitters and the nerve activity, are different in chronic pain patients as compared to persons free of chronic pain. As a result, there is a difference in the pattern of activity in the brain between chronic pain and non-chronic pain patients. Further, studies show that individuals who carry a significant chronic pain load take about a nanosecond more time to process a pain stimulus applied to them as compared to a normal individual free of chronic pain, because there is an increased number of excited or activated neurons.

An important feature of the present invention is therefore to determine the difference in the pattern and/or number of neurons being activated in a chronic pain patient as compared to the activation and patterns of neurons in a normal, chronic pain-free person and, preferably, in a number of persons free of chronic pain (control group).

Additionally, brain (neuron) activity in a chronic pain patient is significantly and statistically meaningfully different from that in a pain-free patient. The brain activity in response to a pain stimulus can therefore be employed to objectively determine and quantify the presence of chronic pain by comparing the patient's brain activities (on an f-MRI) to the brain activities in a pain-free control group (on the standard f-MRI).

DESCRIPTION OF THE PREFERRED EMBODIMENTS

Figure 1:
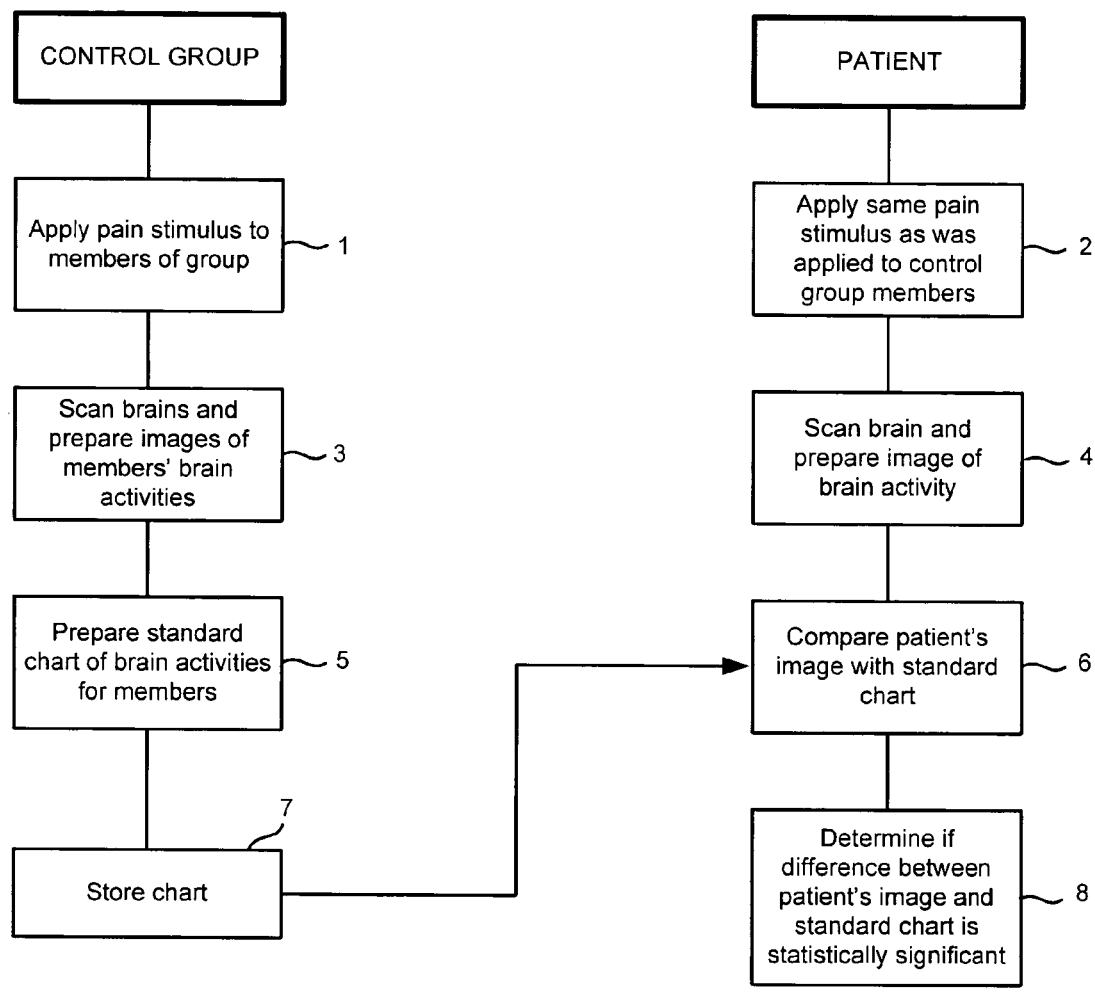
FIG. 1 is a flow diagram of the method for objectively determining if a patient has chronic pain.

Pain that stops activity amounts to a disability. Pain is a subjective, unpleasant sensation that varies, depending on a variety of factors, such as genetics, brain chemistry, past pain experience, culture, emotion, suggestions, etc. Pain can be secondary to actual, potential tissue damage and also secondary to brain abnormal/pathological nociception information processing.

Clinicians, insurance companies and the courts have relied on physical examination and a variety of examination techniques to identify and quantify pain. For example, in the evaluation of chronic pain patients, routine MRI scans, CT scans, electromyelograms, etc. have been employed as providing at least a measure of non-subjective findings, but they are not objective. A routine MRI may show pathology that is or is not a pain generator. The levels of the pain and/or disability stated by a patient are subjective complaints that are highly variable and not objectively reliable. However, on an f-MRI, pain perception by the brain, as distinguished by statements from the patient, can be objectively observed.

The patient may have one or multiple painful body parts, for example. Chronic low back pain is a number one cause of disability in individuals under age 45. After age 45 it is the third leading cause of disability. Body areas that are affected with chronic pain vary, but involve the cervical spine, shoulders, arms, wrists and hands, dorsal and lumbar spine, hips, knees, ankles, entire arms, entire legs, etc. These same anatomical areas are amenable to pain stimulation evaluation by comparing the patient's f-MRI to the standard f-MRI (or "chart") at the same level of pain stimulation applied to the same anatomical areas.

One of the objectives of the present invention is to provide the requesting person or agency (e.g. the insurance company)

with an objective statistical comparison of a patient with ongoing pain to normal pain-free persons. The results are based on the pattern and/or the percentage of neuron activation compared to standard normal pain-free persons when a pain-producing stimulus is applied at or near the suspected pain generator. Alterations and pattern changes will occur in pain processing between normal and chronic pain subjects when the same stimulation is applied such as heat, pressure, vibration or cold to the same anatomic area.

This invention benefits insurance companies, courts, etc. as well as the chronic pain patients themselves. Insurance company studies have shown an estimated 20% to 46% of litigation involving chronic pain and suffering is based on either fraudulent behavior or misrepresentations by the plaintiff. Other insurance company-funded studies have shown that up to approximately 40% of the population feels that it is acceptable to misrepresent their chronic pain and suffering symptomatology in order to obtain a favorable insurance or other settlement.

The invention will also benefit the individual with a considerable chronic pain who was not diagnosed as having chronic pain when evaluated/examined in accordance with past practice. Without objective findings, a chronic pain sufferer will occasionally go without appropriate compensation and/or further medical treatment, even though he/she will have continued pain and significant functional activity restrictions limiting his/her income, decreasing the quality of life, and/or impacting his/her family's future. The present invention can identify patients with significant chronic pain, sort out the embellishers and fraudulent claims, and facilitate proper decision making for the appropriate institution or person.

As discussed above, the pain pattern and neuron activation in the brain of a patient with chronic pain is different from that of normal persons with no such pain. Chronic pain patients have an increased pain sensitivity, hyperalgesia and frequently also a central augmentation of pain. For example, a patient with chronic lower back pain or with fibromyalgia who receives a painful stimulus applied to his/her thumbnail will have an f-MRI that differs from that for the control group when the same pain stimulus is applied. Differences in the brain regions and pattern of neuron activation between the two sets of f-MRIs can be objectively observed. Both the fibromyalgia patient and the chronic lower back pain patient will exhibit extensive common patterns of neuron activation of pain in related cortical areas.

Chronic back pain patients and patients with fibromyalgia require a lower magnitude or intensity of pain stimulation than a pain-free person who received the same pain stimulus. Thus, chronic pain patients require a lesser pain stimulus to activate the same painful response than is required for pain-free persons.

Further, depending on his/her current chronic brain pain burden, patients with ongoing chronic pain will reach a maximum of pain and neuron activation even if the magnitude or intensity of the pain stimulus is increased; that is, an even greater pain stimulus will not lead to greater pain after a maximum pain level has been reached. Thus, as compared to a control group, a given pain stimulus applied to a chronic pain patient leads to increased neuron activation and a greater level of pain as compared to pain-free persons. Conversely, the intensity needed to observe a common pain level on the f-MRI will be less for the chronic pain patient than for the pain-free persons. In addition, the chronic pain patient will normally have a different regional cerebral blood flow as compared to the pain-free control group.

Referring to FIG. 1, the actual evaluation whether a given person claiming to suffer chronic pain in fact has chronic pain is conducted in an f-MRI machine by initially placing the patient in a comfortable position within the bore of the magnet of the machine. The patient's head is immobilized, for example with a vacuum bean bag, a foam headrest and a removable plastic bar across the bridge of the nose, although if there is concern about a tremor or movement, a bite bar can be used instead to hold the head steady, and a pain stimulus 2 is applied while the patient's brain is scanned at 4 and an f-MRI image of the brain activity is taken. To avoid the effect of sensitization, the pain stimulus is applied in a random order. The modality of the stimulus will also be random.

Members of the control group were previously subjected to the same pain stimulus 1 at intervals, initially up to a sensation threshold level which lies just below the pain threshold level, and thereafter to the pain threshold level and, finally, to the maximum tolerable pain level, while their brains are scanned at 3 and f-MRI images thereof are taken. The f-MRI images of the members of the control group are statistically combined at 5 into a standard f-MRI image or chart of the average brain activities of the members of the group. The standard chart is then stored at 7, for example in a computer memory or other suitable memory or storage device.

The same protocol used for the control group is used on the chronic pain patient by preferably applying the pain stimulus to the painful body part and the contralateral body part. It should be noted, however, that for purposes of the present invention the pain stimulus can be applied to parts of the body not affected with chronic pain in order to generate f-MRI images that reflect the presence or absence of chronic pain. During scanning, the patient in the f-MRI machine has access to an alarm so that in the event pain becomes intolerable during testing, he/she can stop the test.

The f-MRIs generated during testing of the chronic pain patient are fed into a computer which preferably includes in its database 7 at least the standard f-MRIs which are relevant to the test in progress. In a preferred embodiment, the computer is appropriately programmed to compare the patient's f-MRI or f-MRIs with the standard f-MRIs at 6 and to appropriately quantify the difference, for example in terms of a percentage difference, which can be further processed and can be used by an evaluator, a physician, an insurance company and the like to judge at 8 whether the patient suffers chronic pain and, if so, to preferably also quantify the chronic pain so that, if appropriate, required compensation can be paid. Alternatively, the comparison of the patient's f-MRI to the standard f-MRI can be done manually, for example by a physician.

Although not necessary for the objective determination of the patient's chronic pain level, in a preferred embodiment of the invention the patient can be asked to rate the perceived pain level while the test is in progress, for example to differentiate between mild pain (25%), slight pain (50%), moderate pain (75%) and severe pain (100%). This subjective pain rating provides helpful verification of the objectively conducted pain level tests. As such, it will preferably also be provided to the requestor, e.g. the insurance company, for review and evaluation. However, the objective determination of the chronic pain level in accordance with the invention is based solely on the above-described comparison of the patient's f-MRI with the standard f-MRI to remove all subjective inputs from the evaluation.

The pain stimulus that is applied to both the members of the control group and the individual patients can be selected from a variety of different technologies, which, moreover, are subject to change as new methods become available. Principally, the pain stimulus is applied to the patient and the members of the control group in similar and preferably in an identical manner. As previously mentioned, the pain stimulus is preferably applied to the area from which the pain originates and to the contralateral side thereof.

The pain stimulus is initially applied at a magnitude so that the sensation perceived by the patient is just below his/her pain threshold level. The pain threshold level is reached when the pain stimulus applied to the patient changes from a mere sensation to perceived pain. Thereafter the pain stimulus is increased past the threshold level and up to a maximum stimulation pain level. At each interval or pain level, at least one complete f-MRI showing the patient's brain activity in response to the applied stimulus is taken. Generally speaking, the pain threshold levels will vary from patient to patient (at least in part depending on the patient's level of chronic pain), and they will dictate the amount of pain stimulus that can be applied to any given patient (or member of the control group). Further, tests stopped at the request of the patient are significant and useful as studies that had to be terminated. Both completed and terminated studies will show a difference in the pain level in the patient's brain for comparison to the corresponding pain level in the standard f-MRI for the control group.

Vibratory devices are useful for applying pain stimuli for eliciting pain responses from inflamed/irritated tissue. Vibratory devices are clinically useful in identifying individuals with discogenic back pain. Vibratory devices also cause pain and discomfort when applied to individuals with SI joint dysfunction, painful joints and painful muscles. MVDs (magneto-mechanical vibrotactile device) placed in the static magnetic field of an f-MRI scanner can be used to generate vibration. The MVDs work on the principle of wire coils with small oscillatory currents in a large static magnetic field. The resulting Lorentz forces can be oriented to generate large vibrations that are easily converted to transitional motion of as much as several centimeters. This vibration can also be converted into oscillating motion. Vibratory frequencies of 1 hz to 130 hz and displacement amplitudes of 0.5 mm to 4 mm will produce a positive vibratory response in inflammation. This device is well-described by Golaszewski, S M, et al., in Neuroimaging 2002, September 17 (1): 421-30, *Functional Magnetic Resonance Imaging of the Human Sensorimotor Cortex Using Noval Vibrotactile Stimulator*, and also described by Graham, S J, published in Magnetic Resonance Medicine, 2001, September 46 (3): 436-42, *New Devices Deliver Somatosensory Stimuli During Functional MRI*.

The MVD will be applied with a very mild amount of pressure to make certain there is good tissue contact. This can be accomplished by using a 1 mm to 2 mm raised 1-2 cm diameter soft round pressure point. In patients with hyperalgesia, application with pressure may not be possible, because of pain, however the f-MRI will show positive findings and a change in the pain threshold compared to the normal pain-free members of the control group.

Heat can be applied as a pain stimulus by using a modified thermal stimulator. This can be a Peltier device, also known as thermal electric (TE) modules. It is a small solid state device that acts as a heat pump. When a direct current is applied, heat is moved from one side of the device to the other. Such devices can be used to apply either heat or cold.

Lasers can be used as a pain stimulus to apply heat to peripheral body parts. A $CO_2$ laser that produces infrared radiation will activate nociceptors in the hand or foot, for example. A thulium-YAG (Yttrium-aluminum-granage) laser will also produce nociception. These lasers act as a pain stimuli without concomitant tactile contact or stimulation. Using lasers will also allow rapid alternation in pain manipulation between each side of the body. The use of lasers for stimulating pain is described by Bingel, U, et al., in Neuroimaging 2003, March 18, (3): 740-8, *Single Trial f-MRI Reveals Significant Contralateral Bias in Response to Laser Pain Within Thalamus and Somatosensory Cortexes*.

Pressure pain may be applied as a stimulus with a tensiometer that has a rounded surface with a 3 cm diameter. Pressure may be applied at 4 to 6 mm of mercury, or the lowest level at which the patient reports a beginning of pain. The pain threshold is typically at about 15 to 18 mm in mercury. Pressure may also be applied using a water actuator.

One or more of vibration, pressure, heat, lasers, light touch and cold are used as a pain stimulus, depending on the clinical situation, the patient, the location of the chronic pain, etc. For example, in long-term unilateral muscle pain there is a significant increase in sensitivity to pressure compared to the homologous contralateral area, but there will be no difference in the outcome of thermal testing. Also, in muscle pain, in the painful area there will frequently be a decreased sensitivity to light touch. For such a case, heat or another non-contact device will normally be the preferred pain stimulus.

Transitory or acute pain also causes pain changes in the central nervous system. Such pain is temporary and the nervous system will return to normal when the pain stops. However, with chronic/ongoing pain, there are continued central nervous system changes in the patient's brain which lead to enhanced brain responses (neuron activity and/or patterns of neuron activity) as compared to what occurs in patients without chronic pain.

Depending on intensity of the stimulus, there is an increase in referred pain. (For example, an intense deep pain stimulus will travel to the spinal cord in the unmyelinated C nerve fibers. With the intense stimulation, neighboring neurons will also become active and a lower pain threshold hyperalgesia will result. With significant stimulation of the spinal cord neurons, an associated burning referred pain will develop. This burning referred pain results in an increased area of pain generation. The increased area of referred pain results in increased stimulus size. The increased size of the pain stimulus results in further neuro changes, which results in even further central nervous system changes.

Figure 2:
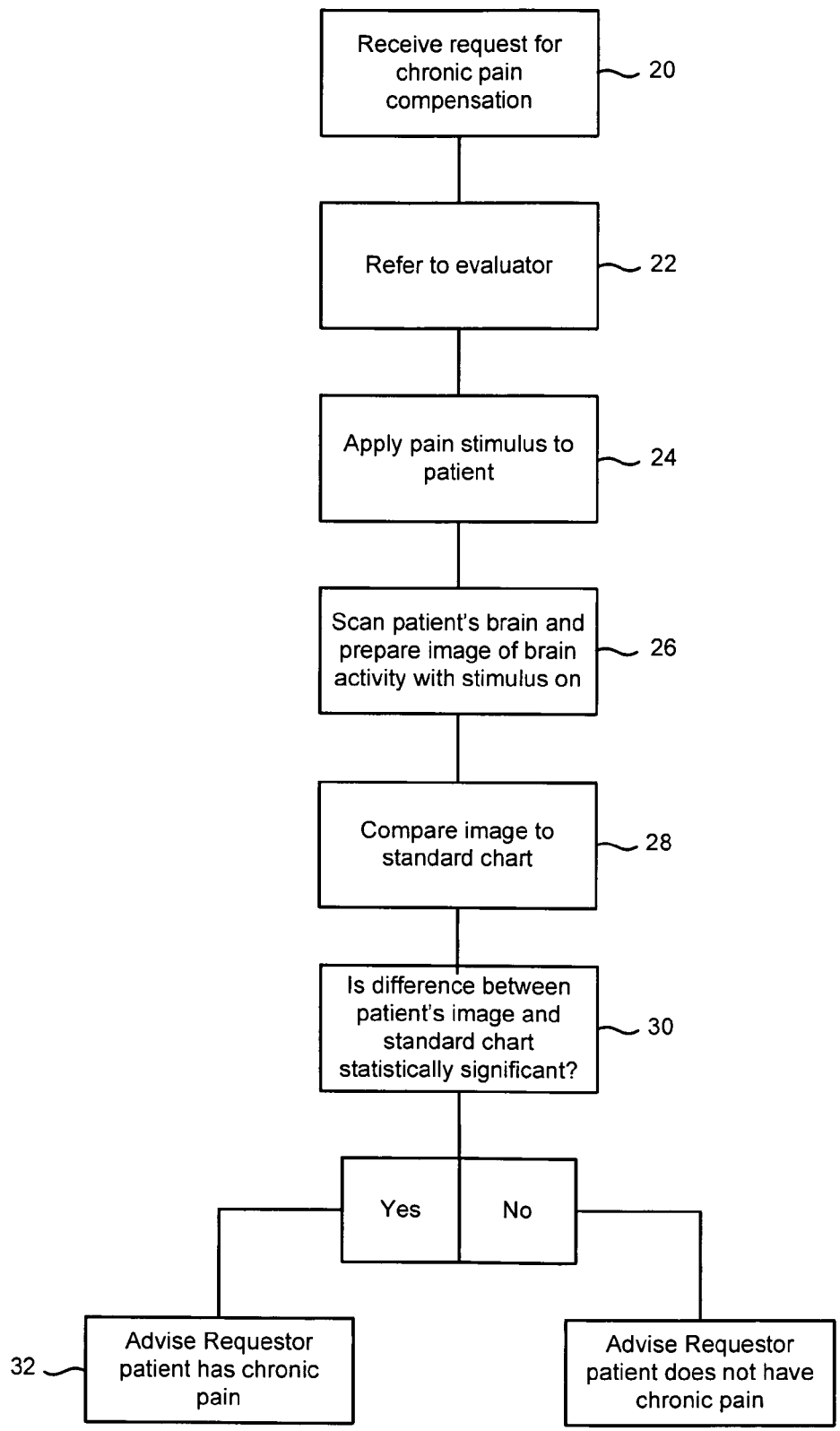
FIG. 2 is a flow diagram which illustrates the processing of a claim for compensation for chronic pain disability.

Referring briefly to FIG. 2, the above-discussed method of the present invention for processing claims by an asserted chronic pain sufferer for reimbursement from an insurance company or any other third party involves initially receiving the request for compensation at 20, for example at an insurance company. The request is referred to an evaluator 22 who then examines the patient by applying pain stimuli to the patient at 24 in the manner described above. With the pain stimulus applied, an f-MRI image of the patient's brain activity is prepared at 26.

The patient's f-MRI is then compared to the standard f-MRI image or chart from the members of the control group at 28, either by a computer (which compares the patient's f-MRI with the standard f-MRI and provides an output that reflects the difference between the two) or, in the alternative, by the evaluator, preferably but not necessarily a physician. At 30, the evaluator judges if the difference between the patient's f-MRI and the standard f-MRI is statistically significant, which means that the differences between the two f-MRIs are sufficiently large so that they are not the result of random variations, but are caused by the presence of chronic pain in the patient. If the difference is judged to be statistically significant, the evaluator informs the requestor at 32 that the patient suffers chronic pain. Conversely, if the difference between the two images is judged to be statistically not significant, the evaluator informs the requestor (e.g. the insurance company) that the patient does not have chronic pain.

Although it is entirely feasible to leave the judgment whether the difference between the two sets of f-MRIs is statistically significant to a computer analysis and use the output (e.g. a numerical output that is reflective of the difference) as the criterion whether the patient suffers chronic pain, for example whenever the difference rises above a predetermined threshold level, review of the respective images by a trained person, such as a physician, will typically be desirable, and he/she may supplement the computer output with additional comments concerning the computer output and/or the testing of the patient and the observed results.

What is claimed is:

1. A method for determining the presence of chronic pain in a patient claiming to suffer chronic pain, comprising applying a pain stimulus to a part of the body of the patient claiming to suffer chronic pain, observing neuron activity in the brain caused by the pain stimulus, comparing observed neuron activity to neuron activity caused by the stimulus when applied to a plurality of persons, wherein each control person is free of pain, and deciding that the patient claiming to suffer chronic pain suffers chronic pain if the neuron activity observed in the patient while the stimulus is applied is judged to be statistically significantly increased from the neuron activity in the plurality of patients who are free of pain, wherein the deciding step is performed without the subjective input from the patient.

2. A method according to claim 1 wherein observing neuron activity in the patient's brain comprises observing physical emissions generated by the brain of the patient.

3. A method according to claim 2 wherein observing physical emissions comprises observing radiofrequency (RF) emissions generated by the brain.

4. A method according to claim 2 wherein observing neuron activity in the RF emissions comprises observing an intensity of the RF emissions and comparing them to an intensity of RF emissions from the plurality of control persons who are free of pain.

5. A method according to claim 3 wherein observing RF emissions comprises observing a pattern of RF emissions generated by the patient's brain, and wherein comparing comprises comparing the observed RF emission pattern in the patient's brain with an RF emission pattern for the control persons who are free of pain.

6. A method according to claim 5 wherein observing patterns of RF emissions includes observing patterns of RF emissions in the patient and in the plurality of control persons who are free of pain in prefrontal areas of the brains.

7. A method according to claim 3 wherein comparing comprises comparing f-MRIs of the patient with a standard f-MRI based on RF emissions by the brains of the control persons who are free of pain.

8. A method according to claim 7 wherein observing neuron activity in the brain of the patient includes generating an f-MRI of RF emissions by the patient's brain.

9. A method according to claim 8 including preparing a standard f-MRI for RF emissions by the brains of control persons who are free of pain which is a statistical summary of the f-MRIs of the control persons who are free of pain, and wherein comparing comprises comparing the f-MRJ of the patient with the standard f-MRI.

10. A method according to claim 9 wherein comparing comprises processing the patient's f-MRI and the standard f-MRI in a computer and generating a computer output which quantifies a difference between the patient's f-MRI and the standard f-MRI.

11. A method according to claim 10 including judging if the difference between the patient's f-MRI and the standard f-MRI is statistically significant.

12. A method according to claim 11 including deciding that the patient has chronic pain if the difference between the patient's f-MRI and the standard f-MRI is statistically significant.

13. A method according to claim 1 wherein comparing comprises preparing a standard chart of brain neuron activity caused by the stimulus in the plurality of control persons who are free of pain, and comparing comprises comparing the neuron activity in the patient's brain with the standard chart.

14. A method according to claim 13 wherein preparing the standard chart comprises comparing a standard f-MRI reflective of the brain neuron activity in the plurality of control persons who are free of pain.

15. A method according to claim 14 wherein the standard f-MRI is an f-MRI of a statistically significant number of control persons who are free of pain.

16. A method according to claim 13 wherein observing the neuron activity in the patient's brain comprises preparing an f-MRI which reflects the neuron activity in the patient's brain, wherein preparing the standard chart includes preparing a standard f-MRI which is reflective of the neuron activity in the brains of the plurality of control persons who are free of pain, and wherein deciding if the patient suffers chronic pain includes judging if a difference between the patient's f-MRI and the standard f-MRI is statistically significant.

17. A method according to claim 16 wherein deciding if the patient suffers chronic pain includes analyzing the difference between the patient's f-MRI and the standard f-MRI with a computer.

18. A method according to claim 17 including generating a computer output which reflects the difference between the patient's f-MRI and the standard f-MRI.

19. A method according to claim 18 wherein the output of the computer is a numerical output.

20. A method according to claim 18 including evaluating the computer output and therewith judging if the patient is likely to have chronic pain.

21. A method according to claim 1 wherein applying the pain stimulus comprises applying at least one of vibrations, pressure, heat, cold and brushing to an external surface of the part of the patient's body.

22. A method for determining if a patient claiming to suffer chronic pain has chronic pain by applying a pain stimulus to the patient, observe neuron activity occurring in the patient's brain in response to the applied pain stimulus, comparing observed neuron activity in the patient's brain to changes caused by the same stimulus in brains of control persons, wherein each control person is without pain, analyzing results from comparing the observed neuron activity in the respective brains to determine if the increase in neuron activity in the patient's brain is statistically significant and, if so, judging that the patient claiming to suffer chronic pain suffers chronic pain, wherein the judging step is performed without the subjective input from the patient.

23. A method according to claim 22 wherein applying comprises applying an external pain stimulus to the patient.

24. A method according to claim 22 wherein comparing comprises preparing an f-MRI of radiofrequency (RE) emissions in the patient's brain while the pain stimulus is applied, preparing a standard f-MRI for the persons without pain by combining individual f-MRIs of neuron activity in the brains of the control persons without pain so that the standard f-MRI is reflective of approximately an average neuron activity in the brains of the control persons without pain, and wherein analyzing comprises evaluating the difference between the patient's f-MRI and the standard f-MRI.

25. A method for determining whether a patient suffers chronic pain comprising
applying a pain stimulus to a plurality of persons who are free of pain and preparing a record reflecting neuron activity in the brain caused by the pain stimulus applied to the persons,
applying the pain stimulus to a patient asserting to have chronic pain,
observing changes in the neuron activity in the brain of the patient caused by the applied pain stimulus,
comparing the observed changes in the neuron activity in the patient's brain with the neuron activity reflected in the record, and
deciding that the patient asserting to have chronic pain has chronic pain if the observed changes in the neuron activity in the patient's brain are statistically significantly different from the neuron activity in the brain reflected by the record, wherein the deciding step is performed without the subjective input of the patient.

26. A method for determining the presence of chronic pain in a patient claiming to suffer chronic pain comprising
generating brain neuron activities in several persons who are free of pain caused by a first pain stimulus applied to the persons,
establishing a non-chronic pain record from the brain neuron activities occurring in the brains of the several pain-free persons,
subjecting a patient suspected of having chronic pain to a second pain stimulus,
observing brain neuron activities in the brain of the patient when the second pain stimulus is applied,
comparing the observed brain neuron activities in the patient to the brain neuron activities reflected by the record, and
determining that the patient claiming to suffer chronic pain suffers chronic pain when the observed brain neuron activities in the patient are statistically significantly different from the brain neuron activities reflected by the record, wherein the determining step is performed without the subjective input of the patient.

27. A method according to claim 26 wherein the first pain stimulus is the same pain stimulus as the second pain stimulus.

28. A method for determining the presence of chronic pain in a patient claiming to suffer chronic pain comprising
applying a pain stimulus to the patient claiming to suffer chronic pain,
observing brain neuron activities in the patient caused by the applied stimulus,
comparing the brain neuron activities to brain neuron activities in a person free of pain to whom the same pain stimulus is applied, and
deciding that the patient claiming to suffer chronic pain suffers chronic pain if the difference in brain neuron activities between the patient and the person is statistically significant, wherein the deciding step is performed without the subjective input of the patient.

29. The method of claim 1, wherein the neuron activity caused by the pain stimulus is observed in a cortical area of the patient's brain.

30. The method of claim 29, wherein the cortical area is selected from the group consisting of prefrontal cortex, somatosensory cortex, and motor cortex.

31. The method of claim 1, wherein the neuron activity caused by the pain stimulus is observed in a somatosensory portion of the patient's brain.

32. The method of claim 1, wherein the neuron activity caused by the pain stimulus is observed in a prefrontal subcortical region of the patient's brain.

33. The method of claim 1, wherein the time required for the patient's brain to process the neuron activity caused by the pain is increased in persons having chronic pain.

34. The method of claim 1, wherein the intensity of the pain stimulus needed to observe a common pain level on an f-MRI is less for a chronic pain patient as compared to the plurality of control persons.

35. The method of claim 1, wherein the pain stimulus is applied to parts of the body not affected with pain.

36. The method of claim 1, wherein the pain stimulus is selected from the group consisting of vibration, pressure, heat, lasers, light touch, and cold.

37. The method of claim 36, wherein the pain stimulus is applied using a vibratory device.

38. The method of claim 36, wherein the pain stimulus is pressure.

* * * * *